US012788547B2

(12) United States Patent
Price et al.

(10) Patent No.: US 12,788,547 B2
(45) Date of Patent: Nov. 10, 2026

(54) STRESS URINARY INCONTINENCE (SUI) DEVICE

(71) Applicant: Liv Labs Inc., Wilmette, IL (US)

(72) Inventors: Carly Rachel Price, Belmont, CA (US); Eric Justin Price, Belmont, CA (US)

(73) Assignee: Liv Labs Inc., Wilmette, IL (US)

( * ) Notice: Subject to any disclaimer, the term of this patent is extended or adjusted under 35 U.S.C. 154(b) by 1040 days.

(21) Appl. No.: 17/727,525

(22) Filed: Apr. 22, 2022

(65) Prior Publication Data

US 2022/0313414 A1 Oct. 6, 2022

Related U.S. Application Data

(63) Continuation of application No. 16/513,167, filed on Jul. 16, 2019, now Pat. No. 11,337,788, which is a (Continued)

(51) Int. Cl.
*A61F 2/00* (2006.01)
*A61N 1/36* (2006.01)

(52) U.S. Cl.
CPC ............ *A61F 2/005* (2013.01); *A61F 2/0009* (2013.01); *A61F 2/0036* (2013.01); *A61N 1/36007* (2013.01)

(58) Field of Classification Search
CPC .............. A61F 2/005; A61F 2210/0014; A61F 2250/0018; A61F 2250/0036; A61F 6/08;
(Continued)

(56) References Cited

U.S. PATENT DOCUMENTS 1,926,518 A 9/1933 Findley
3,080,865 A 3/1963 Vincent
(Continued)

FOREIGN PATENT DOCUMENTS

CN 306557681 5/2021
CN 307313115 5/2022
(Continued)

OTHER PUBLICATIONS

International Search Report and Written Opinion issued by the International Searching authority for application No. PCT/US2017/068969, dated Mar. 6, 2018, 7 pages.
(Continued)

*Primary Examiner* — Christine H Matthews
(74) *Attorney, Agent, or Firm* — COOLEY LLP

(57) ABSTRACT

Urinary incontinence devices generally include a body configured to be inserted into a vagina. The body may have a proximal insertion portion, a plurality of legs coupled to and extending distally from the insertion portion, and a distal retrieval portion. The plurality of legs may each have a length, a width, and a distal end, and the distal ends of the plurality of legs may be coupled together. The body may have a compressed configuration, an expanded configuration, and a lateral cross-sectional diameter, and the lateral cross-sectional diameter of the body may be largest at the widest point of each of the plurality of legs. Methods of treating urinary incontinence may include loading a urinary incontinence device into an applicator, inserting the applicator into the vagina, advancing the incontinence device out of the applicator to position a distal end of the device past the pelvic floor, and removing the incontinence device from the vagina using the distal retrieval portion.

20 Claims, 14 Drawing Sheets

Related U.S. Application Data continuation of application No. PCT/US2017/068969, filed on Dec. 29, 2017.

(60) Provisional application No. 62/499,427, filed on Jan. 24, 2017.

(58) Field of Classification Search
CPC . A61F 2/0036; A61F 2/0009; A61F 13/47227
See application file for complete search history.

(56) References Cited

U.S. PATENT DOCUMENTS

| | | | | |
|---|---|---|---|---|
| 3,372,695 | A | 3/1968 | Beliveau et al. | |
| 3,554,184 | A | 1/1971 | Habib | |
| 3,646,929 | A | 3/1972 | Bonnar | |
| 3,705,575 | A | 12/1972 | Edwards | |
| 4,019,498 | A | 4/1977 | Hawtrey et al. | |
| 4,031,886 | A | 6/1977 | Morhenn | |
| 4,139,006 | A | 2/1979 | Corey | |
| 4,307,716 | A | 12/1981 | Davis | |
| 4,875,898 | A | 10/1989 | Eakin | |
| 4,920,986 | A | 5/1990 | Biswas | |
| 5,007,894 | A | 4/1991 | Enhorning | |
| 5,036,867 | A | 8/1991 | Biswas | |
| 5,224,494 | A | 7/1993 | Enhorning | |
| 5,386,836 | A | 2/1995 | Biswas | |
| 5,483,976 | A * | 1/1996 | McLaughlin | A61M 31/00 128/885 |
| 5,603,685 | A | 2/1997 | Tutrone, Jr. | |
| 5,618,256 | A | 4/1997 | Reimer | |
| 5,771,899 | A | 6/1998 | Martelly et al. | |
| 5,785,640 | A | 7/1998 | Kresch et al. | |
| 5,813,973 | A | 9/1998 | Gloth | |
| 6,013,023 | A | 1/2000 | Klingenstein | |
| 6,090,038 | A | 7/2000 | Zunker et al. | |
| 6,090,098 | A | 7/2000 | Zunker et al. | |
| 6,095,969 | A | 8/2000 | Karram et al. | |
| 6,142,928 | A | 11/2000 | Zunker et al. | |
| 6,158,435 | A | 12/2000 | Dorsey | |
| 6,311,689 | B1 | 11/2001 | Tihon | |
| 6,413,206 | B2 | 7/2002 | Biswas | |
| 6,418,930 | B1 | 7/2002 | Fowler | |
| 6,460,542 | B1 | 10/2002 | James | |
| 6,503,190 | B1 | 1/2003 | Ulmsten et al. | |
| 6,530,879 | B1 | 3/2003 | Adamkiewicz | |
| 6,558,370 | B2 | 5/2003 | Moser | |
| 6,645,136 | B1 | 11/2003 | Zunker et al. | |
| 6,645,137 | B2 | 11/2003 | Ulmsten et al. | |
| 6,676,594 | B1 | 1/2004 | Zunker et al. | |
| 6,679,831 | B1 | 1/2004 | Zunker et al. | |
| 6,739,340 | B1 | 5/2004 | Jensen et al. | |
| 6,770,025 | B2 | 8/2004 | Zunker | |
| 6,808,485 | B2 | 10/2004 | Zunker | |
| D500,938 | S | 1/2005 | Lee | |
| 6,969,380 | B1 | 11/2005 | Zunker | |
| 7,036,511 | B2 | 5/2006 | Nissenkorn | |
| 7,056,278 | B2 | 6/2006 | Adamkiewicz | |
| 7,070,585 | B2 | 7/2006 | Jensen | |
| 7,179,219 | B2 | 2/2007 | Matlock | |
| 7,351,195 | B2 | 4/2008 | Farrell | |
| 7,673,631 | B2 | 3/2010 | Astani et al. | |
| 7,717,892 | B2 | 5/2010 | Bartning et al. | |
| 7,771,344 | B2 | 8/2010 | Ziv | |
| 7,779,843 | B2 | 8/2010 | Astani et al. | |
| 7,892,163 | B2 | 2/2011 | Bartning et al. | |
| 7,935,098 | B2 | 5/2011 | Bartning et al. | |
| 7,981,021 | B2 | 7/2011 | Spitz et al. | |
| 7,998,056 | B2 | 8/2011 | Stifter et al. | |
| 8,047,980 | B2 | 11/2011 | Bartning et al. | |
| D650,089 | S | 12/2011 | Kleyman | |
| 8,127,768 | B2 | 3/2012 | Ziv | |
| 8,177,706 | B2 | 5/2012 | Bartning et al. | |
| 8,221,374 | B2 | 7/2012 | Hou et al. | |
| 8,302,608 | B2 | 11/2012 | Harmanli | |
| 8,449,446 | B2 | 5/2013 | Ziv et al. | |
| 8,617,047 | B2 | 12/2013 | Sinai et al. | |
| 8,651,109 | B2 | 2/2014 | Ziv et al. | |
| 8,727,961 | B2 | 5/2014 | Ziv | |
| 8,888,676 | B2 | 11/2014 | Ziv et al. | |
| 8,911,344 | B2 | 12/2014 | Altan et al. | |
| 9,017,382 | B2 | 4/2015 | Ogdahl | |
| 9,022,919 | B2 | 5/2015 | Ellefson et al. | |
| 9,050,183 | B2 | 6/2015 | Bartning et al. | |
| 9,072,578 | B2 | 7/2015 | Herbowy et al. | |
| 9,078,726 | B2 | 7/2015 | Karapasha | |
| 9,173,768 | B2 | 11/2015 | Bartning et al. | |
| 9,198,748 | B2 | 12/2015 | Ziv et al. | |
| 9,277,982 | B2 | 3/2016 | Zunker et al. | |
| 9,339,361 | B2 | 5/2016 | Ziv et al. | |
| 9,339,364 | B2 | 5/2016 | Durling et al. | |
| 9,357,982 | B2 | 6/2016 | Edmunds | |
| 9,439,748 | B2 | 9/2016 | Durling et al. | |
| 9,445,882 | B2 | 9/2016 | Henriksson et al. | |
| 9,532,907 | B1 | 1/2017 | Agrawal | |
| 9,549,798 | B2 | 1/2017 | Sinai et al. | |
| 10,039,666 | B2 | 8/2018 | Ziv et al. | |
| D885,602 | S | 5/2020 | Dumler et al. | |
| 11,185,438 | B2 | 11/2021 | Sopher et al. | |
| D949,365 | S | 4/2022 | Li | |
| D950,759 | S | 5/2022 | Lee et al. | |
| 11,337,788 | B2 | 5/2022 | Price et al. | |
| 11,491,047 | B2 | 11/2022 | Sopher et al. | |
| 11,576,811 | B2 | 2/2023 | Ziv et al. | |
| D999,030 | S | 9/2023 | Krus et al. | |
| D1,012,306 | S | 1/2024 | Cantu | |
| 11,865,033 | B2 | 1/2024 | Maier et al. | |
| D1,071,181 | S | 4/2025 | Price et al. | |
| 2004/0249238 | A1 | 12/2004 | Farrell | |
| 2008/0033230 | A1 | 2/2008 | Bartning et al. | |
| 2008/0033231 | A1 | 2/2008 | Bartning et al. | |
| 2008/0149109 | A1 | 6/2008 | Ziv | |
| 2008/0214984 | A1 | 9/2008 | Caracci et al. | |
| 2008/0281149 | A1 | 11/2008 | Sinai et al. | |
| 2009/0095304 | A1 | 4/2009 | Richardson et al. | |
| 2009/0203959 | A1 | 8/2009 | Ziv et al. | |
| 2009/0266367 | A1 | 10/2009 | Ziv et al. | |
| 2011/0065980 | A1 | 3/2011 | Ziv et al. | |
| 2011/0160525 | A1 | 6/2011 | Zunker et al. | |
| 2012/0164601 | A1 | 6/2012 | Ellefson et al. | |
| 2012/0165599 | A1 | 6/2012 | Ellefson et al. | |
| 2012/0165601 | A1 | 6/2012 | Ellefson et al. | |
| 2012/0259167 | A1 | 10/2012 | Karapasha et al. | |
| 2012/0271098 | A1 | 10/2012 | Ziv et al. | |
| 2013/0025604 | A1 * | 1/2013 | Harmanli | A61F 6/08 128/834 |
| 2014/0100416 | A1 | 4/2014 | Durling et al. | |
| 2015/0320536 | A1 | 11/2015 | Deitch | |
| 2016/0015500 | A1 | 1/2016 | Ziv et al. | |
| 2017/0049609 | A1 | 2/2017 | Conti | |
| 2017/0086956 | A1 | 3/2017 | Sarto et al. | |
| 2019/0336260 | A1 | 11/2019 | Price et al. | |
| 2024/0407941 | A1 | 12/2024 | Arabin | |

FOREIGN PATENT DOCUMENTS

| | | | |
|---|---|---|---|
| EP | 2376020 | B1 | 1/2017 |
| EP | 9180409 | S | 9/2022 |
| JP | 1781366 | S | 10/2024 |
| KR | 301232936 | | 9/2023 |
| WO | WO 2008/079271 | A1 | 7/2008 |
| WO | WO 2012/141940 | A2 | 10/2012 |
| WO | WO 2018/140192 | A1 | 8/2018 |

OTHER PUBLICATIONS

International Preliminary Report on Patentability issued by the International Searching authority for application No. PCT/US2017/068969, dated Jul. 30, 2019, 6 pages.

Extended European Search Report issued by the European Patent Office for Application No. 17894083.9, dated Oct. 1, 2020, 6 pages.

Author Unknown, "female internal vaginal devices," continenceproductadviser.org, [Post date Oct. 20, 2020], [Site seen:

(56) References Cited

OTHER PUBLICATIONS

Mar. 13, 2024], Seen at URL: https://www.continenceproductadvisor.org/femaledevices, 2 pages.
Coo-Wee: Triple Pack, Coo wee, [Post date: Mar. 29, 2023], [Site seen: Mar. 13, 2024], seen at URL: https://coowee.me/products/coo-wee-tri pie-pack-1, 2 pages.
Daily use Vaginal Pessary, LivLabs, [Post date unknown], [Site seen Mar. 13, 2024], Seen at URL: https://www.livlabsfitness.com/ products. 1 page.
Efemia bladder support, imedicare, [Postdarte Nov. 30, 2023], [Site seen: Mar. 13, 2024], Seen at URL: https://www.mypelvichealth.co.uk/ en/women/urine-leakage-management/efemia-bladder-support-product/1an-efemia-bladder-support-starter-kit/, 2 pages.
Office Action for Australian Application No. AU2017395751, mailed Oct. 13, 2022, 5 pages.
"Female Continence Devices," [online] Continenceproductadvisor.Org, Oct. 20, 2020, [Retrieved from the Internet at URL:[www.continenceproductadvisor.org/femaledevices]; 2 pages.
"Meet PIPPA," Labs Fitness, (date unknown), [Retrieved from the Internet on Jan. 8, 2026, at URL: https://livlabsfitness.com]; 4 pages.
Youtube, "The Most Cost Effective and Environmentally Sustainable Bladder Support Pessary Solution: Efemia," [online] iMEDicare Ltd, Dec. 18, 2025, [Retrieved from the Internet at URL: https://www.youtube.com/watch?v=spuT RF5shg]; 1 page.

* cited by examiner

STRESS URINARY INCONTINENCE (SUI) DEVICE

CROSS-REFERENCE TO RELATED APPLICATIONS

This application is a continuation of U.S. patent application Ser. No. 16/513,167, filed Jul. 16, 2019, which is a continuation of International Patent Application No. PCT/US2017/068969, filed on Dec. 29, 2017, which claims priority to U.S. Patent Application Ser. No. 62/499,427, filed on Jan. 24, 2017, each of which is hereby incorporated by reference in its entirety.

TECHNICAL FIELD

Described here are devices, systems, and methods for treating female urinary incontinence.

BACKGROUND

Urinary incontinence is a common issue for women. It is estimated that one in three women leak urine involuntarily, and that approximately 25% of women will seek medical advice for the condition at some point, typically after suffering with it for several years. The most common form of incontinence is "stress urinary incontinence." Stress incontinence is the involuntary leaking of urine which occurs during exercise, sneezing, coughing, and laughing. During these activities, the abdominal muscles apply pressure to the bladder and urethra, and a combination of weakened pelvic floor muscles and urethral hypermobility allows urine leakage to occur. Stress incontinence effects women age 35-65, particularly after vaginal childbirth when the muscles of the pelvic floor are stretched and weakened. Other causes are aging, from pen-menopause into menopause, and obesity.

There are two common treatments for stress incontinence: exercises to strengthen the pelvic floor (Kegel exercises) or surgery. While Kegel exercises are helpful, they require daily repetition and dedication, and the exercises need to be done properly and for an indefinite amount of time to be effective. Many women are unsure how to do the exercises, or are not motivated to stick with them. Even if women do Kegel exercises regularly, it is difficult for most to regain full strength of the pelvic floor, and the frequency of their leaking may diminish, but still occur.

Physical therapy services, to train women to properly do Kegel exercises and strengthen the pelvic floor are not commonly available outside of major cities, and many women with stress incontinence would prefer to avoid elective surgery.

Many women are forced to use incontinence pads, or even menstrual pads, to address their urinary incontinence. Pads, however, are a poor solution for several reasons: they can be cumbersome and uncomfortable, undignified to use (e.g., like wearing a diaper) and expensive over time. In addition, they create a lot of waste and have a negative environmental impact.

While pessaries do exist, there is little consumer awareness of them as a solution for SUI, and most require a prescription from a doctor and need to be fitted. Some are uncomfortable or painful in use and/or tend to fall out of the vagina, which make them an undesirable solution. Additionally, some pessaries are designed for a single-use, and thus are wasteful and expensive. Thus, additional devices for treatment of female urinary incontinence are desirable.

BRIEF SUMMARY

Described here are devices, systems, and methods for treatment of urinary incontinence. In some embodiments, urinary incontinence devices described here may comprise a body configured to be inserted into a vagina. The body may comprise a compressed configuration, an expanded configuration, and a lateral cross-sectional diameter. The body may further comprise a proximal insertion portion, a plurality of legs that may be coupled to and may extend distally from the insertion portion, and a distal retrieval portion. Each leg may have a length, a width, and a distal end, and the distal ends of the plurality of legs may be coupled together forming a distal surface. The distal retrieval portion may be coupled to the distal surface. Additionally, in the expanded configuration, the lateral cross-sectional diameter of the body may be largest at the widest portion of each of the plurality of legs.

In some variations, urinary incontinence devices may comprise a body configured to be inserted into a vagina. The body may comprise a longitudinal axis, a proximal solid portion, a central hollow portion, and a distal portion. The central hollow portion may comprise a plurality of elongate legs that may extend distally from the proximal portion to a common distal intersection. Each of the plurality of legs may be curved along the longitudinal axis and may comprise the same cross-sectional shape. A maximum cross-sectional width of each of the plurality of legs may decrease along the longitudinal axis from a proximal end to a distal end of each leg. The distal portion may be coupled to and may extend distally from the distal intersection. The distal portion may comprise an opening configured to assist in removal of the device from the vagina.

In some instances, urinary incontinence devices may comprise a body configured to be inserted into a vagina and the body may comprise a compressed configuration, an expanded configuration, and a longitudinal axis. The body may further comprise a proximal insertion portion, a support portion comprising a plurality of elongate legs, and a distal retrieval portion. The plurality of elongate legs may be coupled to and may extend distally from the insertion portion to a common distal intersection. Each leg may be curved radially outward in the expanded configuration. The support portion may comprise a hollow interior. The distal retrieval portion may be coupled to and may extend distally from the support portion. A length of the support portion may be at least double a length of the proximal insertion portion in the expanded configuration.

In some embodiments, urinary continence devices may comprise a body configured to be inserted into a vagina. The body may comprise a longitudinal axis, a proximal insertion portion, a plurality of legs, and a distal retrieval portion. The plurality of legs may each comprise a proximal end, a distal end, and a longitudinal axis. The proximal end of each leg may be coupled to the insertion portion and the distal ends of the plurality of legs may be coupled to one another. Each leg may curve radially outward along its longitudinal axis between its proximal and distal ends. The longitudinal axis of each of the plurality of legs may be substantially parallel to the longitudinal axis of the body.

Also described here are methods of treating stress urinary incontinence in a user having a vagina and a pelvic floor. In some variations, the methods may comprise loading a urinary incontinence device into an applicator, inserting the applicator into the vagina, advancing the incontinence device out of the applicator to position a distal end of the device past the pelvic floor, and removing the incontinence device from the vagina. In some variations, the urinary incontinence device may be reusable and/or the applicator may be reusable. In some instances, the methods may further comprise re-loading the incontinence device into the applicator, and reinserting the applicator into the vagina. The urinary incontinence device may comprise a proximal insertion portion, a support portion comprising a plurality of radially expandable legs, and a distal retrieval portion. The incontinence device may be in a compressed configuration when loaded in the applicator. In some variations, advancing the incontinence device may cause it to self-expand to the expanded configuration and push against the urethra. Additionally, the incontinence device may be removed from the vagina using the distal retrieval portion.

BRIEF DESCRIPTION OF THE DRAWINGS

FIG. 9A depicts a variation of a urinary incontinence device being loaded into an applicator, FIG. 9B depicts insertion of the urinary incontinence device shown in FIG. 9A, and FIG. 9C depicts removal of the urinary incontinence device shown in FIG. 9A.

DETAILED DESCRIPTION

Figure 1A:
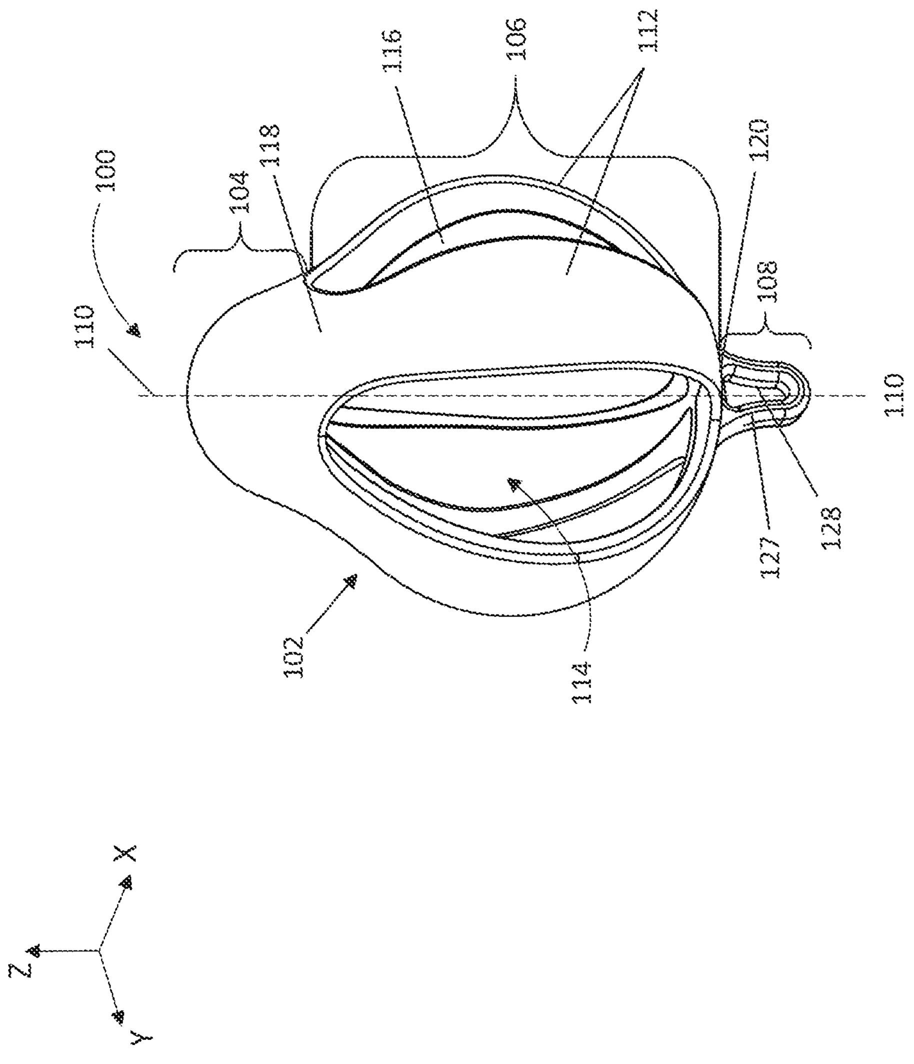
FIGS. 1A-1C depict a perspective view, a side view, and a top view, respectively, of a variation of a urinary incontinence device.

Described here are devices, system, and methods for treating urinary incontinence, for example, stress urinary incontinence. The devices described here may be configured to be inserted into the vagina to apply a force to or around the urethra to support and/or close the urethra, thus reducing the occurrence of urine leaks. The devices may also apply a force to or around the bladder (e.g., the bladder neck) to the lift the bladder, which may also assist in reducing the occurrence of leaks. The devices may be collapsible and expandable, such that they may be inserted with an applicator in a collapsed configuration and expanded within the vaginal canal at an appropriate location, for example, beneath the cervix and past the pelvic floor (e.g., about 3-5 cm into the vagina for most women, however, insertion length varies based on anatomy). In some variations, the devices and applicators described here may be reusable, for example, over a three month, six month, or twelve month period.

I. Devices

Generally, the urinary incontinence devices described here may comprise a body configured to be inserted into a vagina and comprising a proximal portion, a central portion comprising a plurality of legs and a plurality of gaps, and a distal portion. The proximal portion may be located on an insertion end of the device and the distal portion may be located on a retrieval end of the device, with the central portion located between the proximal and distal portions. The central portion may generally be hollow, which may decrease the weight of the device, thus assisting in maintaining the device within the vagina, and additionally allowing for aeration and/or fluid transfer through the device. The device may be configured to apply a closure force to the urethra and/or a lifting force to the bladder (e.g., the bladder neck), one or both of which may decrease the incidence of urine leaks. The closure force may be a radial force (e.g., a force applied about 90 degrees from the longitudinal axis of the device). In some variations, the body may additionally comprise force concentrators such as protrusions, ridges, or otherwise raised portions, which may assist in focusing the radial force or pressure in a particular location within the vagina (e.g., between the urinary sphincter (at the bladder neck) and the pelvic floor), which may localize the force needed to minimize or prevent incontinence and may assist in holding the device in place.

The device may generally be collapsible such that is has a lower profile for insertion (for example, using an applicator), and expandable, such that it may apply a sufficient force to close the urethra and/or lift the bladder once inserted. The body of the device may be shaped to self-orient within the vagina and maintain a desired position once inserted. The device may have different flexural properties along its longitudinal axis such that different portions or regions of the device may be specifically tailored for particular uses, for example, insertion, anchoring, resistance to torsional bending, lifting, applying radial force, removal, and the like, as will be explained in more detail below. Additionally, the device and/or applicator may be configured to be reusable.

Body

As mentioned above, the devices described here may comprise a body configured to be inserted into a vagina. The body may comprise a proximal or insertion portion, a plurality of legs coupled to, or integrally formed with, and extending distally from the insertion portion, and a distal or retrieval portion. In some variations, the body may be monolithic (e.g., have a single-piece construction), while in other variations, one or more of the insertion portion, legs, and retrieval portion may be formed separately and attached to form the body. The body may have any shape suitable for positioning it within the vagina and effectively applying force to the urethra and/or the bladder to minimize or prevent urinary incontinence. For example, in some variations, the body may comprise or otherwise form a spherical shape, a pear shape, a diamond shape, an egg shape or ovoid, a peanut shape, an elliptical or ellipsoid shape, an hourglass shape, a tear drop shape, a combination thereof, or the like. In some variations, the body may comprise a circular, oval, pear, diamond, rectangular, tear drop, or peanut shaped longitudinal cross-sectional shape and a circular or oval lateral cross-sectional shape. Moreover, in some variations, the body may be symmetrical along a central longitudinal axis and/or may be asymmetrical along a central lateral axis (where the lateral axis is perpendicular to the longitudinal axis).

Figure 1C:
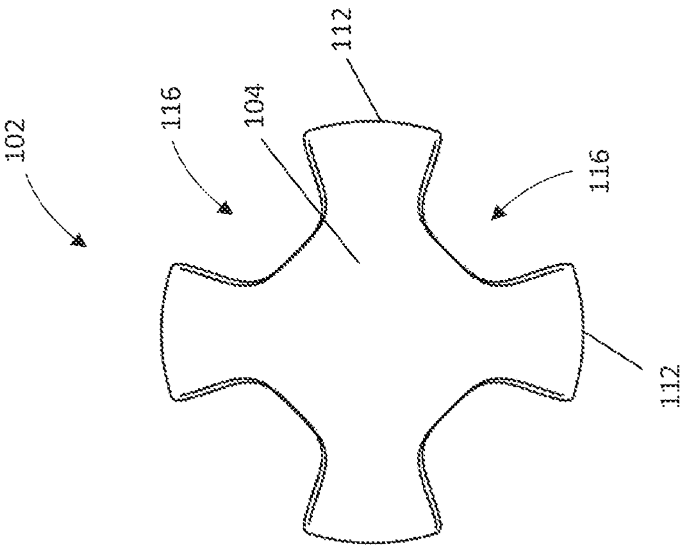
Figure 1B:
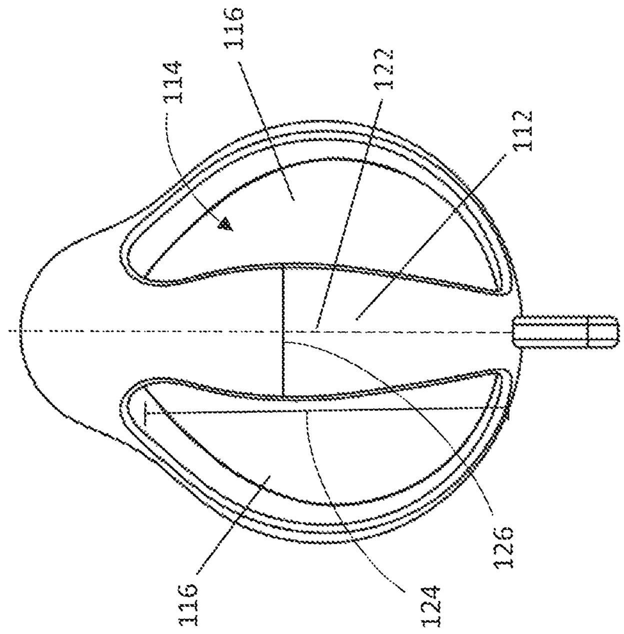

FIGS. 1A-1C depict perspective, side, and top views, respectively, of a variation of a urinary incontinence device 100 comprising a generally pear shaped body 102. The body 102 may comprise a proximal insertion portion 104, a central support portion 106, and a distal retrieval portion 108. The central support portion 106 may be coupled to (including integrally formed with), and may extend distally from, the insertion portion 104, and the distal retrieval portion 108 may be coupled to (including integrally formed with), and may extend distally from, the central support portion 106. The proximal insertion portion 104 may be configured to assist in inserting the body 102 into the vagina and appropriately positioning the device relative to the bladder, the urethra, and the urethral sphincter. The central support portion 106 may be configured to apply a closure force to the urethra and/or a lifting force to the bladder such that urine leakage is minimized or eliminated. The distal retrieval portion 108 may be configured to assist a user in locating and removing the body 102 from the vagina after use.

Proximal Portion

As mentioned above, the insertion portion 104 may be configured to assist a user in inserting the body 102 into the vagina. For example, the insertion portion 104 may be generally rounded, dome-shaped and/or hemispherical. In some variations, the insertion portion 104 may comprise a generally circular cross-sectional shape along the X-Y plane. The generally circular cross-sectional area of the insertion portion in the X-Y plane may decrease proximally along the longitudinal axis 110 of the device (i.e., along the Z-axis). In some variations, such as the variation depicted in FIGS. 1A-1C, the insertion portion 104 may be solid, which may provide added stiffness and resistance to distortion and/or torsional bending (i.e., to minimize or prevent twisting) to the top or proximal end of the body 102 relative to the central and distal portions 106, 108. The insertion portion 104 may also be smooth. The shape, radius of curvature, and/or stiffness of the insertion portion 104 may assist a user in inserting and positioning the incontinence device 100 within the vagina.

The insertion portion 104 may have any suitable length or transverse dimension (e.g., diameter). For example, in some variations, the insertion portion 104 may have a length between about 5 mm and about 20 mm or between about 8 mm and about 12 mm. Additionally or alternatively, the insertion portion 104 may have a maximum transverse dimension (e.g., diameter) between about 5 mm and about 30 mm or between about 15 mm and about 20 mm. As mentioned above, in some variations, the transverse dimension or diameter (and thus cross-sectional area) may vary along the length of the insertion portion 104, but need not. In variations in which the transverse dimension and cross-sectional area vary along the length, the maximum transverse dimension and area may be at the distal end of the insertion portion 104.

Central Portion

The central support portion 106 may comprise a plurality of legs, elongate elements, or struts 112 surrounding or otherwise forming a hollow interior or chamber 114. Thus, the central support portion 106 may be hollow. Moreover, the central support portion 106 may further comprise a plurality of gaps or spaces 116 formed between the plurality of legs 112 (i.e., there may be a gap or space 116 between and separating each of the plurality of legs 112). The gaps or spaces 116 may be fluidly coupled with the chamber 114 such that gases and fluids may pass through the central support portion 106 and thus the body 102 when in use. Thus, in some variations, the gaps or spaces 116 may form or otherwise serve as fluid channels. The gaps or spaces 116 may have any suitable shape, for example, they may be oval, diamond shaped, rectangular, circular, or the like. Additionally, it may be beneficial for the central support portion 106 and thus, in some variations, the majority of the body 102, to be hollow. This may reduce the weight of the body 102 and therefore decrease the likelihood that the device 100 will become dislodged, shift, or fall out during use, especially during periods of high activity (e.g., exercise) or high stress (e.g., sneezing). Thus, minimizing the weight of the device may provide for increased retention of the device in use, particularly during physical activity and may also provide for increased comfort. In some variations, the central support portion 106 may further comprise a straight, central, longitudinal support (e.g., along the central longitudinal axis 110 of the body 102) or post coupled between the proximal and distal ends of the plurality of legs 112 and positioned within or traversing through the chamber 114. In these variations, the longitudinal support may provide additional longitudinal and torsional stiffness without adding radial stiffness.

Each of the plurality of legs 112 may comprise a proximal end 118, a distal end 120, and may have a longitudinal axis 122, a length 124, and a width 126. The proximal end of each leg 112 may be coupled to the insertion portion (e.g., integrally formed with or formed separately and attached) and the distal ends 120 of the legs 112 may be coupled to one another. For example, in some variations, the distal ends 120 of the legs 112 may be coupled together forming a distal surface or a common distal intersection. The longitudinal axis 122 formed between the proximal and distal ends of each leg 112 (e.g., in the compressed or expanded configuration) may be substantially parallel to (e.g., not transverse to), and off-set from, the longitudinal axis 110 of the body 102 and the longitudinal axis of each of the other legs 112 such that the legs 112 do not twist, rotate, tilt, or otherwise angle between the proximal and distal portions 106, 108 of the body 102. Put another way, the legs 112 may travel in a straight path between the proximal and distal portions 106, 108 such that the proximal end 118 of each leg 112 is longitudinal aligned with the distal end 120 of each leg 112. Utilizing legs that travel in a straight path may provide several benefits, including but not limited to providing lateral support to the urethra and ease of manufacturing (e.g., greater degree of freedom in selecting appropriate manufacturing process). Each of the plurality of legs 112 may be curved radially outward along the longitudinal axis 122 and the longitudinal axis 110 of the body 102 in the expanded configuration, which will be explained in more detail below. For example, each of the plurality of legs 112 may be convex along its length and the length of the body 102. In some variations, a plurality, but not all, of the legs 112 may be curved radially outward or convex along each leg's length (e.g., one or more legs may be straight/uncurved or may be curved radially inward or be concave along its length).

The devices described here may comprise any suitable number of legs 112 and/or gaps or spaces 116, for example, two, three, four, five, six, seven, eight, or more, and the legs 112 and gaps 116 may have any suitable dimensions. For example, in some variations, the central portion 106 may comprise four legs 112 and four gaps 116. Each of the plurality of legs 112 and/or gaps 116 may be elongate such that the length 124 of each leg 112 and/or gap 116 may be larger than its respective width. In some variations, one or more of the plurality of legs 112 may have a length 124 between about 20 mm and about 70 mm or between about 30 mm and about 40 mm. Additionally or alternatively, in some variations, one or more of the plurality of gaps 116 may have a length between about 20 mm and about 70 mm or between about 30 mm and about 40 mm.

The width 126 of each of the plurality of legs 112 may vary along the longitudinal axis 110 of the device 100 and the longitudinal axis 122 of the respective leg 112. For example, in some variations, the width 126 of one or more of the legs 112 (including all of the legs 112) may increase from the proximal end 118 to the distal end 120, or vice versa. In some variations, the width 126 of one or more of the legs 112 may be greatest along a central lateral axis of the body 102, and may decrease toward both the proximal and distal ends 118, 120 of the legs 112. In some instances, the width 126 of one or more of the legs 112 may be greatest at the center of the leg, may be second greatest at the proximal end 118, and may be third greatest at the distal end 120. In some variations, such as that depicted in FIG. 1B, one or more of the legs 112 may be widest (e.g., have the greatest width 126) where the lateral cross-sectional diameter of the body 302 is largest in the expanded configuration. Put another way, the width 126 of one or more of the plurality of legs 112 may be greatest when the body 102 or the central portion 106 has the greatest diameter along the X-Y plane in the expanded configuration.

Figure 2D:
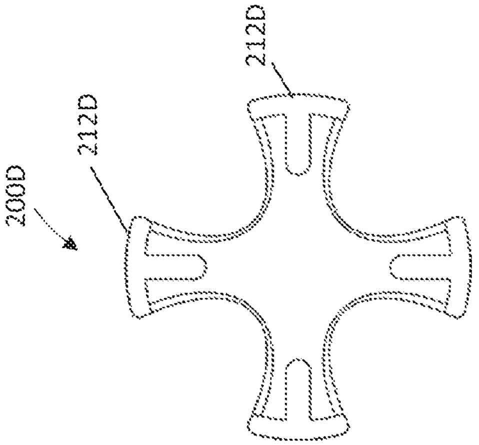
FIGS. 2B-2D depict variations of the cross-sectional shape of the legs of the urinary incontinence device in FIG. 2A.
Figure 2C:
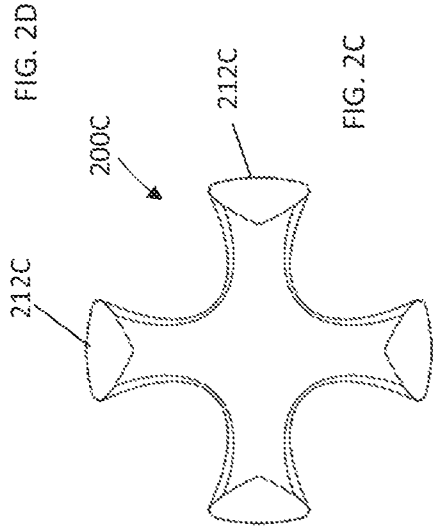
Figure 2B:
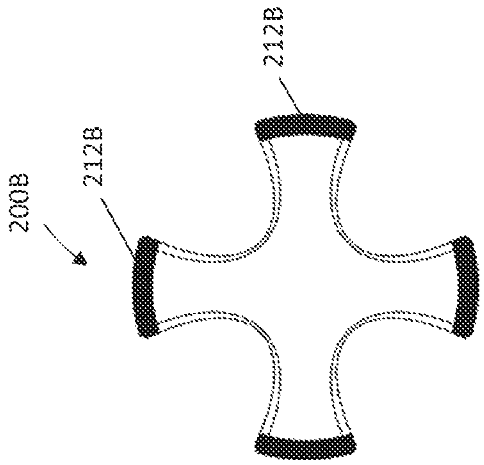

Each of the plurality of legs 112 may be configured (for example, may have a particular cross-sectional shape and/or be formed of one or more particular materials) to atraumatically apply force radially outward (i.e., perpendicular to the longitudinal axis 110 of the body 102), provide rigidity along the longitudinal axis 110 of the body 102, and provide general resistance to torsional bending. In some variations, the cross-sectional shapes of the plurality of legs 112 may be selected such that the legs may be fit together or otherwise compressed into a cylindrical or other lower profile shape in the compressed configuration, as will be described in more detail below. FIGS. 2B-2D depict cross-sectional views of an exemplary incontinence device 200 along line A-A of FIG. 2A. As shown there, the exemplary incontinence devices 200B, 200C, 200D may each comprise a plurality of legs 212B, 212C, 212D. When looking at the cross-sectional view, the plurality of legs 212B, 212C, 212D may comprise a slightly curved or arced rectangular shape (FIG. 2B), a triangular or wedge shape (FIG. 2C), or a T-beam shape (FIG. 2D). In other variations, the plurality of legs may comprise a circular, elliptical, I-beam, C-shaped, trapezoidal, or curved trapezoidal cross-sectional shape. In some variations, each of the plurality of legs may have the same general cross-sectional shape, while in other variations, one or more of the plurality of legs may have generally different cross-sectional shapes. The general cross-sectional shape of each leg may be constant along the longitudinal axis or length of each leg (e.g., generally triangular or generally trapezoidal, even if the dimensions of the shape change) or of the body, while in other variations, the cross-sectional shape of each leg may vary along its longitudinal axis or length of each leg (e.g., generally triangular to generally circular or rectangular) or of the body.

Each of the plurality of legs 112 may be configured to have different properties (e.g., flexibility/stiffness, resistance to torsion, applied radial force, weight) along its longitudinal axis 122 or length 124. Utilizing legs 112 with different properties along the longitudinal axis 122 or length 124 of the legs 112 or the body 102 may provide a number of benefits, including but not limited to, a tailored force profile that results in localized force to close the urethra (e.g., into or around a gelatinous region of the urethra) and/or lift the bladder, easier insertion and removal, increased flexibility in particular portions of the device which may result in increased comfort, ability for the device to self-orient relative to anatomical structures, and an increased ability for the device to remain in the inserted position.

For example, in some variations, the cross-sectional shape, thickness, area, and/or widths, may vary along the longitudinal axis 122 or length 124 of each leg 112, or of the body 102, which may result in different moments of inertia, stiffness, bending, and/or force profiles along the length of each leg 112. In some variations, each of the plurality of legs 112 may be constructed to have the same properties relative to each of the other legs 112, while in other variations, one or more of the plurality of legs 112 may be constructed to have different properties than one or more of the other of the plurality of legs 112. In some embodiments, one or more of the plurality of legs 112 may comprise one or more indentations and/or slits (e.g., vertical, horizontal, angled) in an external and/or internal (e.g., facing toward or adjacent to the chamber 114) surface of the legs 112, which may further vary the flexibility of the legs. In some variations, the flexibility of the legs may vary as a function of the expansion and compression of the device. For example, the flexibility of the legs may decrease when the crenellated portions of the legs interfere mechanically with one another as the device is moved from an expanded configuration to a compressed configuration. Moreover, as will be explained in more detail below, one or more of the legs 112 may additionally or alternatively comprise force concentrators on an external surface of the legs 112, which may also vary the flexibility/rigidity of the legs 112 and/or the force/pressure applied by the legs 112 to tissue in use. One or more (including all) of the plurality of legs 112 may comprise tapered, radiused, or chamfered longitudinal edges, which may provide additional comfort and prevent the device from catching or otherwise damaging tissue.

Figures 3A, 3B, 3C, 3D:
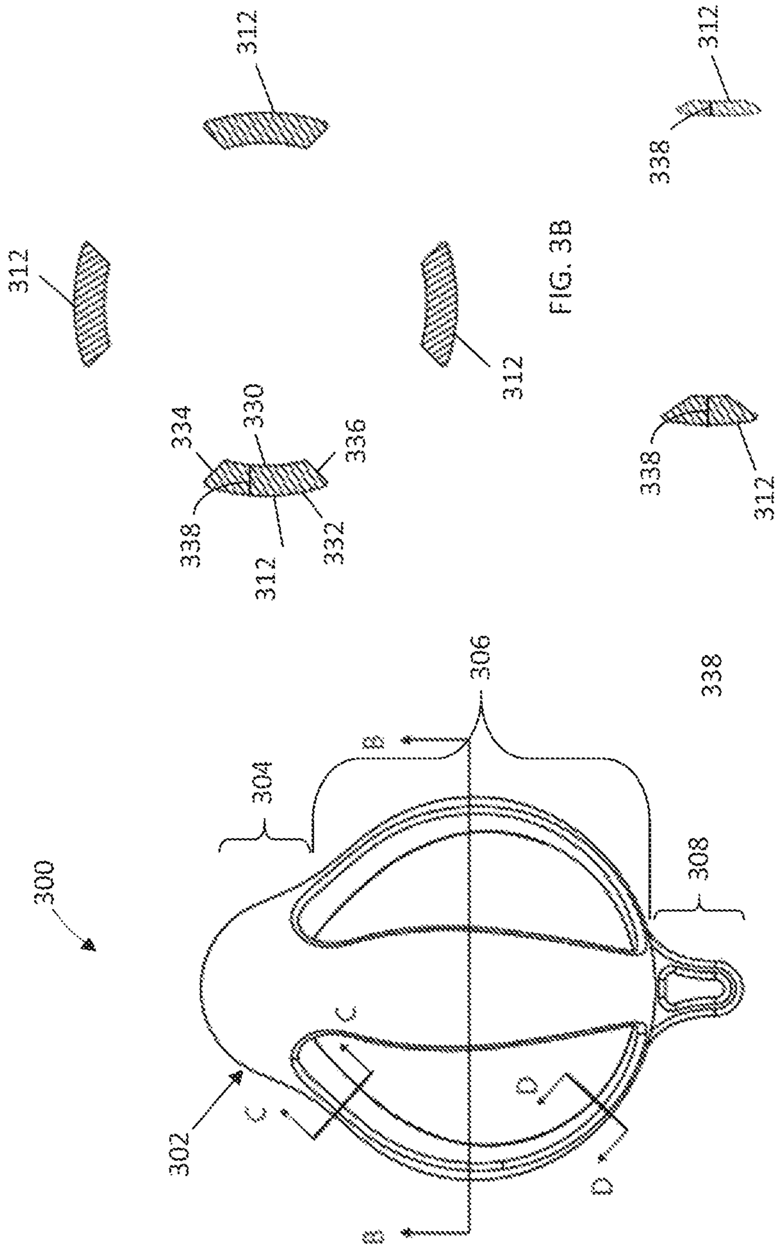
FIG. 3A depicts a side view of a variation of a urinary incontinence device and FIGS. 3B-3D depict cross-sectional views of a leg(s) of the incontinence device in FIG. 3A at various locations.

FIGS. 3A-3F depict an exemplary embodiment of a urinary incontinence device 300 having a body 302 comprising a proximal portion 304, a central portion 306 comprising a plurality of legs 312, and a distal portion 308. FIGS. 3B, 3C, and 3D depicted cross-sectional views of one or more of the legs 312 along lines B-B, C-C, and D-D respectively. In particular, FIG. 3B depicts a cross-sectional view of the four legs 312 of the incontinence device 300 along a central lateral axis, FIG. 3C depicts a cross-sectional view of one of the four legs 312 in a proximal region of the central portion 306, and FIG. 3D depicts a cross-sectional view of one of the four legs 312 in a distal region of the central portion 306.

As can be seen from comparing FIGS. 3B-3D, the cross-sectional characteristics of the legs 312 may vary along the longitudinal axis/length of each leg and the longitudinal axis of the device 300. For example, the maximum cross-sectional width or thickness 338 of each leg 312 may decrease from the proximal region of the central portion 306 to the distal region of the central portion 306. In other variations, the thickness 338 may increase from the proximal region of the central portion 306 to the distal region of the central portion 306, or the thickness 338 may be greatest along the central lateral axis and may decrease both proximally and distally. In still other variations, the thickness 338 may be greatest along the central lateral axis, second greatest in the proximal region of the central portion 306, and third greatest in the distal region of the central portion 306. In some variations, it may be beneficial for the thickness 338 to be greatest in the proximal region of the central portion 306 and decrease distally as this may provide increased rigidity at the proximal end of the device to assist in insertion, efficient and targeted closing and/or lifting forces in the central portion, and enough flexibility for comfort. This configuration may also make removal of the device easier.

The cross-sectional area and/or moment of inertia of each leg 312 may also vary along the longitudinal axis or length of each leg 312 and the longitudinal axis of the device 300. For example, the cross-sectional area and/or moment of inertia may decrease from the proximal region of the central portion 306 to the distal region of the central portion 308 or vice versa, or the cross-sectional area and/or moment of inertia may be greatest along the central lateral axis and may decrease both proximally and distally. In still other variations, the cross-sectional area and/or moment of inertia may be greatest along the central lateral axis, second greatest in the proximal region of the central portion 306, and third greatest in the distal region of the central portion 306. The variations may also allow devices to adapt to a wider range of human geometries, such as may occur from normal anatomical variations.

Additionally, the characteristics of the cross-sectional shape the legs 312 may also vary along the longitudinal axis of the device 300 and the longitudinal axis or length of the legs 312. For example, each of the legs may have the same cross-sectional shape and the general shape may remain the same along the longitudinal axis/length of each leg, but the particularities or the dimensions of the shape may change. Turning to the embodiment depicted in FIGS. 3B-3D, each of the legs 312 may have the same cross-sectional shape (e.g., a curved or modified trapezoid, segmented ring-shape) and the general shape may remain the same along the longitudinal axis/length of each leg (e.g., the shape remains a quadrilateral, generally trapezoidal, generally forming a segmented ring), the particularities of the shape may change. For example, in variations in which the shape is generally trapezoidal (including curved trapezoidal) the length of one or both of the bases 330, 332 and/or one or both of the legs 334, 336 of the modified trapezoid may vary (e.g., increase from the proximal region to the distal region of the central portion 306, decrease from the proximal region to the distal region of the central portion 306, be largest along the central lateral axis and decrease proximally and distally, be largest along the central lateral axis, be second largest in the distal region, and third largest in the proximal region).

Additionally, the radius of curvature of one or both of the bases 330, 332 and/or the angle formed between the bases 330, 332 and the legs 334, 336 may also vary along the longitudinal axis/length of the legs 312. For example, in some variations, the radius of curvature of one or both bases 330, 332 may increase or decrease from the proximal region to the distal region of the central portion 306, or the radius of curvature of one or both bases 330, 332 may be largest along the central lateral axis, second largest at the proximal region, and third largest at the distal region. In other variations, the radius of curvature of one or both bases 330, 332 may be constant along the longitudinal axis/length of the legs 312, or may be largest along the central lateral axis and the same in the proximal and distal regions of the central portion 306.

It should be appreciated that FIGS. 3B-3D depict one variation of the incontinence device 300, and that in other variations, the legs 312 may have a different cross-sectional shape (e.g., rectangular, triangular, circular, elliptical, T-beam). In these variations, the particularities and/or dimensions of those cross-sectional shapes may vary similarly to the variations described with respect to the embodiment depicted in FIGS. 3B-3D (e.g., the cross-sectional area, radius of curvature, maximum transverse dimension, height, major and/or minor axis, moment of inertia, or the like may vary as described above).

Figure 3F:
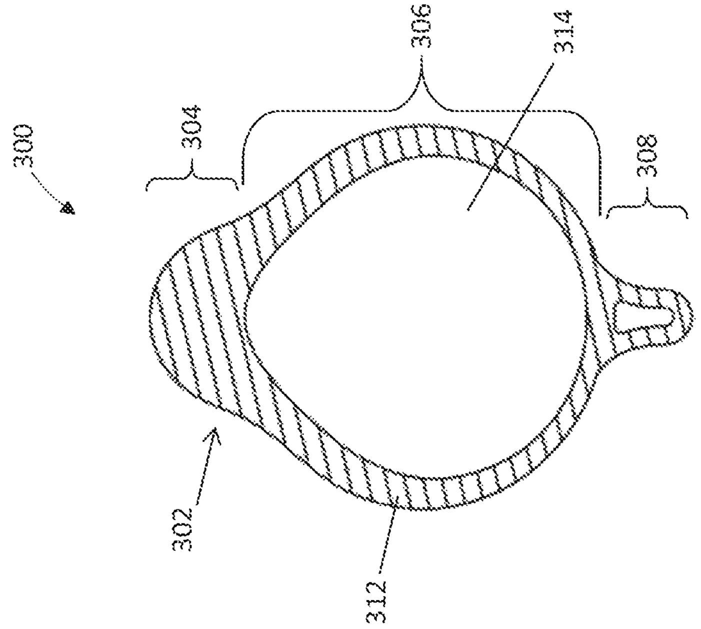
FIGS. 3E and 3F depict a top view and a longitudinal cross-sectional view, respectively, of the incontinence device shown in FIG. 3A.
Figure 3E:
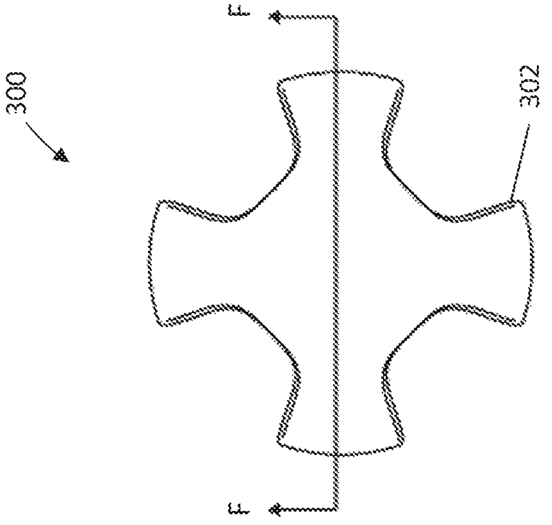

FIGS. 3E and 3F depict top and longitudinal cross-sectional views of the incontinence device 300 of FIGS. 3A-3D. In particular, FIG. 3F depicts a cross-sectional view of the device 300 along line F-F. As can be seen there, the thickness of the body 302 may decrease distally from the proximal end of the incontinence device 300 to the distal end. In particular, the thickness of the body 302 in the proximal portion 304 may be greater than the thickness of the body 302 in the central portion 306, which may be greater than the thickness of the body 302 in the distal portion 308. Additionally, the thickness of one or more of the plurality of legs 312 (including all of the legs 312) may decrease along the longitudinal axis of the device 300/body 302 from the proximal end of the leg 312 to the distal end or from the proximal to distal regions of the central portion 306. As mentioned above, it may be desirable to configure the body 302 and/or plurality of legs 312 such that the thickness decreases along a longitudinal axis of the body 302/device 300 and the legs 312 as this may provide an effective combination of rigidity, flexibility, and closure and/or lifting force such that the device is efficacious, comfortable, and easy to insert and remove. Also depicted in FIG. 3F is the hollow interior or chamber 314 of the central portion 306 of the body 302. As depicted there, chamber 314 may be generally egg-shaped or have a generally ovoid cross-sectional shape. Utilizing a central portion 306 with a hollow interior or chamber 314 may provide many benefits, including but not limited to, decreased weight, additional flexibility, aeration when in use, ability for secretions to pass through the device 300 when in use, and cleanability after or between uses.

Additionally or alternatively, the body 302 may be constructed using different materials to tailor the rigidity, flexibility, and/or force profiles of the body 302. For example, in some variations, the proximal portion 304 may comprise a first material, the central portion 306 may comprise a second material, and the third portion 308 may comprise a third material, where the flexibility, modulus of elasticity, or durometer may vary between the first, second, and third materials. For example, the first material may have the highest durometer/be the least flexible and the durometer may decrease from a proximal to a distal end of the body 302. In other variations, the proximal portion 304 may comprise a first material and the second and third portions 306, 308 may comprise a second material, where the first material may have a higher durometer/be less flexible than the second material. In some instances, the material may vary along the longitudinal axis/length of the legs 312 within the central portion 306. For example, in some variations, the proximal end of the legs 312 may be harder/less flexible than the distal end, or vice versa. In some embodiments, the flexibility of the legs 312 may decrease from a proximal end of the legs 312 to the distal end or from a proximal region of the central portion 306 to the distal region, or vice versa.

In some variations, the body 302, or any portion thereof (e.g., proximal, central, distal portions) may comprise a first material that forms a core of the body 302 or portion thereof, and a second material surrounding or otherwise covering the first material or core. In these variations, the first material forming the core may be harder/less flexible than the second material forming the covering such that first material provides longitudinal rigidity, resistance to torsion, and an effective radial force profile, while the second material assists with comfort and flexibility. For example, in some variations, the core may comprise metal or thermoplastic and a softer material (e.g., thermoset or thermoplastic) may be overmolded. In some variations, a combination of materials may be utilized for the core such that the properties (e.g., bending, force profile, rigidity, resistance to torsion) may be adjusted and tailored along the longitudinal axis of the device, for example, in different portions of the body 302. In some instances, different portions of the device may comprise similar materials, e.g., silicones, but with different durometers (stiffness). Varying the cross-sectional areas and/or materials as described may provide the desired device performance (e.g., application of force to the urethra) while preserving comfort (e.g., atraumaticity) and minimizing the weight of the device.

Distal Portion

Turning back to FIG. 1A, the distal retrieval portion 108 may be coupled to (including integrally formed with) and/or extend distally from the central portion 106 (e.g., a distal end of the central portion 106, the distal ends of the plurality of legs 112). In some variations, the distal retrieval portion may be coupled to and/or extend distally from a distal surface or distal intersection formed from coupling together the plurality of legs 112. The distal retrieval portion 108 may be configured to assist a user in locating, retrieving, and/or removing the device from the vagina. For example, the distal retrieval portion may comprise a handle that may be grasped by a user to pull the device from the vagina. The handle may comprise an elongate structure or extension 127 that may be held with a user's fingers. The elongate structure or extension 127 may comprise any suitable cross-sectional shape, for example, circular, semi-circular, rectangular, oval, triangular, pear shaped, U-shaped, and the like. In some variations, the elongate structure 127 may be rounded (e.g., in the form of a cylinder), or may be flat (e.g., have flat sides as depicted in FIG. 1A). Additionally, the distal portion (e.g., the handle) may be smooth, comprise rounded edges, and may be otherwise atraumatic, which may minimize the risk of the distal portion (e.g., the handle/elongate structure 127) poking the user or causing discomfort.

The distal retrieval portion 108 may further comprise elements that may assist a user in gripping the device, for example, an opening, such as opening 128 depicted in FIG. 1A, ridges, protrusions, grooves, indentations, a textured surface, a combination thereof, or the like. In some variations, a string or retrieval tether, cable, or flexible elongate member, may be positioned through the opening, which may further assist a user in accessing the device when inserted. Additionally, the opening may further be used to hang the device to dry after cleaning it. In some embodiments, the device may not comprise a distal retrieval portion. In these variations, a string or other flexible elongate member may be threaded through the spaces or gaps 116 between the legs 112 and this flexible elongate member may be grasped by a user to remove the device.

Compressed and Expanded Configurations

As mentioned briefly above, the body of the incontinence devices described here may be compressible and expandable. For example, the body may comprise a compressed, low-profile, delivery configuration for insertion, and an expanded, larger-profile, deployed configuration for use. The body may be resilient, self-expandable, and/or biased toward the expanded configuration (e.g., radially outward) such that additional expansion elements may not be needed to expand the body in the deployed configuration. In some variations, the body may be formed of or comprise a material that may compress at least 3:1, and in some variations, at least or more than 4:1, from the expanded configuration to the compressed configuration without permanent deformation. Examples of materials that may be used include but are not limited to thermoplastic elastomers (such as urethanes, thermoplastic vulcanizates including EPDM rubbers, thermoset elastomers (like silicone), thermoplastics (such as polypropylene (PP) and polyethylene (PE)), multiphase alloys such as a nickel-cobalt based alloy, spring-tempered steel, a combination thereof, or the like. In some instances, it may be beneficial to utilize elastomers due to their high degree of stretchability or extensibility, which may allow the device to stretch more than 10% of its length without tearing. This may assist in preventing damage to the device during normal handling and use.

Figure 4A:
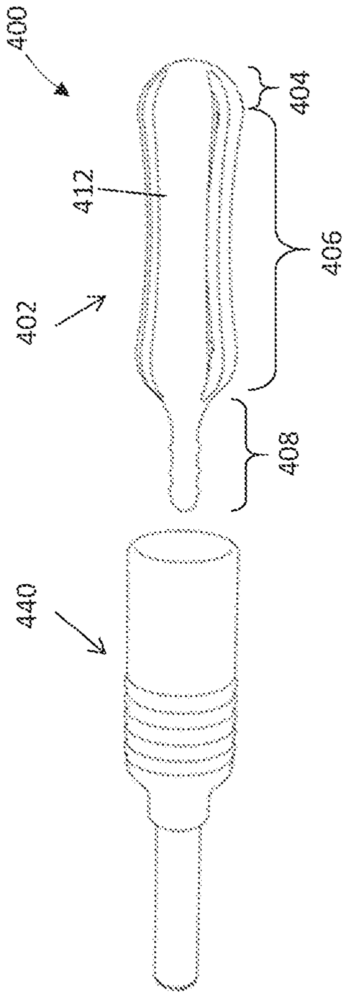
FIGS. 4A and 4B depict a variation of a urinary incontinence device in a compressed configuration outside and inside an applicator, respectively.
Figure 4B:
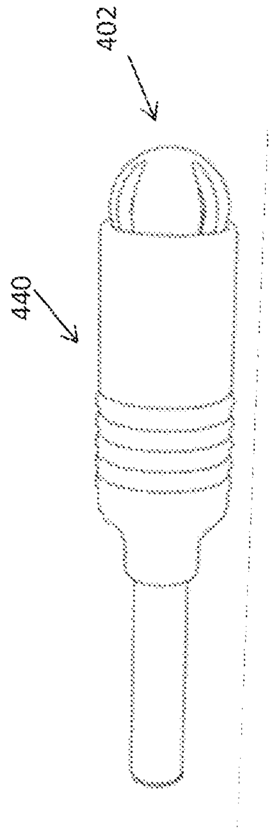

FIGS. 4A and 4B depict a variation of a urinary incontinence device 400 comprising a body 402. The urinary incontinence device 400 is depicted in a compressed configuration outside of an applicator 440 in FIG. 4A and depicted positioned within the applicator 440 for insertion in FIG. 4B. Variations of the applicator 440 will be described in additional detail herein. Examples of urinary incontinence devices in an expanded configuration can be seen in FIGS. 1A, 2A, and 3A. As can be seen in FIG. 4B, in some variations, all or part of the proximal portion of the body may extend from a proximal end of the applicator when the body is positioned within the applicator. In other variations, a smaller part of the proximal portion (e.g., only the proximal end surface) of the body may extend from the proximal end of the applicator, or no part of the body may extend from the applicator (i.e., the entire body fits within the applicator).

The cross-sectional diameter of one or more portions of the body may be smaller in the compressed configuration than in the expanded configuration. As can be seen most clearly in FIG. 4A, in the compressed configuration, the central portion 406 of the body 402 may have a smaller diameter in the compressed configuration than in the expanded configuration. In some variations, the proximal portion 404 may have the same diameter in the compressed and expanded configurations, and the diameter of the proximal portion 404 may set the minimum diameter for the body 402 and the device 400 in the compressed configuration. In other variations, the diameter of the proximal portion 404 may also be smaller in the compressed configuration. The distal portion 408 may have the same diameter or dimensions in the compressed and expanded configurations or may have a smaller diameter or dimensions in the compressed configuration. In some variations, the body 402 may expand radially outward along the entire length of the central portion when moving from the compressed configuration to the expanded configuration.

When in the compressed configuration, the chamber in the central portion 406 formed by the plurality of legs 412 may be smaller (e.g., have a smaller diameter or transverse dimension, have a smaller cross-sectional area) than when the body 402 is in the expanded configuration. Additionally, the size (e.g., width, cross-sectional area) of the gaps formed between the legs 412 may also decrease. Put another way, the plurality of legs 412 may be closer to one another and in some variations, may be touching, when the device 400 is in the compressed configuration. Moreover, the overall length of the body 402 may increase in the compressed configuration as compared with the expanded configuration.

In some variations, the legs 412 may be configured (e.g., shaped) to interface or mate with one another in the compressed configuration to enable the central portion 406 of the body 402 to form a cylindrical shape with a smaller diameter. This may enable the device 400 to be inserted using an applicator with a relatively small diameter and a smaller diameter than the diameter of the central portion in the expanded configuration. It may be beneficial to configure the plurality of legs 412 to nicely fit together into a smaller diameter cylinder (or other shape) as this may make it easier for a user to insert and position the device in the applicator.

Figure 2A:
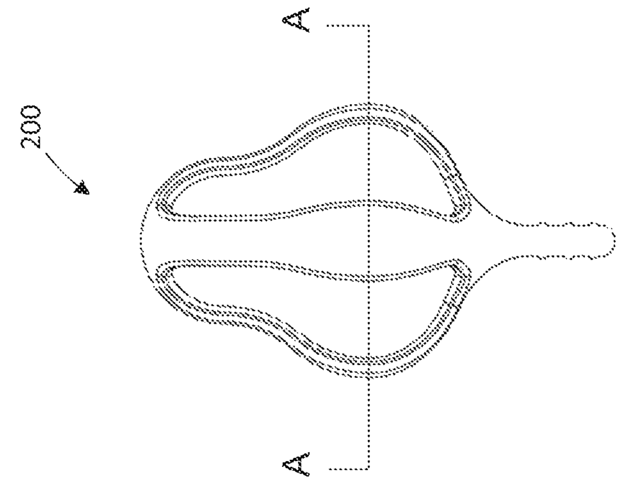
FIG. 2A depicts a side view of a variation of a urinary incontinence device.

In the expanded configuration, as depicted in FIGS. 1A, 2A, and 3A, the central portion may have a larger diameter than when the device is in the compressed configuration. For example, in some variations, the largest diameter of the central portion may be between about 20 mm and about 80 mm and/or about 2×, about 2.5×, about 3×, between about 2× and about 3×, or between about 2.5× and about 3× greater than the largest diameter of the central portion in the compressed configuration.

Body Shape

As mentioned above, the body of the incontinence devices described here may have a variety of different shapes. For example, as described above and depicted in FIG. 1A, the body may have a pear shape comprising a first bulbous portion (e.g., a proximal hemispherical or substantially hemispherical portion) and a second bulbous portion (e.g., a spherical or substantially spherical portion). The first and second bulbous portions may be interconnected or otherwise attached to form a pear shape. In some variations, such as the variation depicted in FIG. 1A, the first bulbous portion may correspond to or be within the proximal portion of the body and the second bulbous portion may correspond to or be within the central portion of the body. In other variations, such as the variation depicted in FIGS. 5A-5B, the first and second bulbous portions may correspond to or be within the central portion of the body.

The lengths of the first and second bulbous portions may be different. In some variations, the length of the first bulbous portion may be less than the length of the second bulbous portion. For example, the first bulbous portion may be between about 5 mm and about 30 mm, between about 5 mm and about 20 mm, between about 7 mm and about 15 mm, between about 5 mm and about 10 mm, or about 10 mm in length, while the second bulbous portion may be between about 20 mm and about 50 mm, between about 30 mm and about 50 mm, between about 35 mm and about 45 mm, or about 45 mm in length. In some variations, the length of the second bulbous portion may be between about 40 mm and about 80 mm. In some instances, the length of the second bulbous portion may be between about 1.5× and about 2× (double), between about 1.5× and about 3× (triple), between about 2× and about 3×, at least about 3×, at least about 2×, or at least about 1.5× a length of the first bulbous portion. Thus, in variations in which the first bulbous portion corresponds to the proximal portion and the second bulbous portion corresponds to the central portion, the length of the central portion may be between about 40 mm and about 80 mm, may be between about 1.5× and about 2× (double), between about 1.5× and about 3× (triple), between about 2× and about 3×, at least about 3×, about 3×, at least about 2×, about 2×, at least about 1.5×, or about 1.5× the length of the proximal portion. In some variations, the central portion and/or second bulbous portion may have the same or a similar length (e.g., about 40 mm) as the "target" proximal/mid-urethral area (e.g., about 30-40 mm), which may assist in providing adequate coverage to that area.

Additionally, the diameter (e.g., diameter along X-Y plane, maximum diameter, maximum transverse dimension) of the first and second bulbous portions may also be different. For example, the maximum diameter of the first bulbous portion may be less than the maximum diameter of the second bulbous portion. In some variations, the maximum diameter of the first bulbous portion may be between about 10 mm and about 30 mm or between about 15 mm and about 20 mm, and the maximum diameter of the second bulbous portion may be between about 30 mm and about 90 mm or between about 35 mm and about 60 mm. In some instances, the maximum diameter in the second bulbous portion may be between about 2× and about 3×, between about 2× and 4×, about 2×, about 3×, or about 4× greater than the maximum diameter in the first bulbous portion. Accordingly, in variations in which the first and second bulbous portions correspond with the proximal and central portions, the maximum diameter of the central portion may between about 30 mm and about 90 mm or between about 35 mm and about 60 mm and/or at least about 2× greater than the maximum diameter of the proximal portion. Additionally, in some variations, the maximum diameter of the second bulbous portion may be greater than a diameter of the vaginal opening, which may assist in preventing unwanted or premature expulsion of the body from the vagina.

Additionally, the lengths of the first and second bulbous portions may vary in different embodiments relative to the length of the body, with or without the distal portion. For example, in some variations, the first bulbous portion may be about ⅕, about ¼, or between about ⅕ and about ¼ the length of the body including the distal portion, and/or may be about ¼, about ⅓, or between about ¼ and about ⅓ the length of the body not including the distal portion. In some instances, the second bulbous portion may be about ⅔, about ¾, or between about ⅔ and about ¾ the length of the body including the distal portion, and/or may be about ⅔, about ¾, or between about ⅔ and about ¾ the length of the body not including the distal portion. Accordingly, in variations in which the first and second bulbous portions correspond with the proximal and central portions, the proximal portion may be about ⅕, about ¼, or between about ⅕ and about ¼ the length of the body including the distal portion, and/or about ¼, about ⅓, or between about ¼ and about ⅓ the length of the body not including the distal portion (i.e., combined length of proximal and central portions). Additionally, in these variations, the central portion may be about ⅔, about ¾, or between about ⅔ and about ¾ the length of the body including the distal portion, and/or about ⅔, about ¾, or between about ⅔ and about ¾ the length of the body not including the distal portion.

Additionally, the first and second bulbous portions may each form convex outer surfaces or regions along the length of the body and may be interconnected or coupled at a concave outer surface or region. Thus, in some variations, the body may comprise a first convex portion at or near the proximal end of the body and a second convex portion at or near a center of the body, and a concave portion between the first and second convex portions. The first and second convex portions may comprise different radii of curvature, for example, the first convex region may have a smaller radius of curvature than the second convex portion, or vice versa. Additionally, the concave region may have a different radius of curvature than one or both of the convex regions, which may, for example, be greater than or less than the radii of curvature of one or both of the convex regions.

For example, in the variation depicted in FIG. 1A, the body 102 may comprise a first convex region in the proximal portion 104 of the body 102, a second convex region in the central portion 106 of the body 102, and a concave region between the first and second convex regions. As shown there, the radius of curvature of the concave region may be greater than the radius of curvature of the second convex region, which may be greater than the radius of curvature of the first convex region. In other variations, for example the variation depicted in FIGS. 5A and 5B, the radius of curvature of the second convex region may be greater than the radius of curvature of the concave region, which may be greater than or equal to the radius of curvature of the first convex region.

The convex and concave portions of the body may assist in properly positioning the device and may provide closure and/or lift forces to minimize and/or eliminate urine leakage. For example, in some variations, the convex and concave portions of the body may assist in positioning the device between the bladder and the pelvic floor, and more specifically, underneath the bladder and adjacent the urethral sphincter in the curved region of the urethropelvic ligament or endopelvic fascia that forms the posterior urethra-vesical angle. The first convex and concave regions may be configured to fit within the posterior urethra-vesical angle, which may appropriately position the device for application of one or both of a closure force to the urethra and a lift force to the bladder neck, and may assist in holding the device in place within the body. In some variations and in some users, the concave portion and/or a proximal portion of the second convex portion may apply a lifting force to the bladder, which may aid in minimizing and/or preventing urinary incontinence. Additionally or alternatively, the central portion of the second convex region may apply a closure force to the urethra, which may aid in minimizing and/or preventing urinary incontinence. In some variations and in use with some users, the devices described here may be configured to apply both a lifting force to the bladder and a closure force to the urethra.

Thus, in variations in which the first convex region corresponds to or is within the proximal portion of the body and the concave and second convex regions are within the central portion of the body, the proximal and central portions may be configured to assist in positioning the device and applying a lifting and/or closure force, as described above with respect to the convex and concave regions. In variations in which the convex and concave regions correspond to or are within the central portion of the body, the central portion may both assist in positioning the device and in applying a lifting and/or closure force, as described above with respect to the convex and concave regions. Additionally, in some variations, the maximum diameter of the second convex region may be greater than a diameter of the vaginal opening, which may assist in preventing unwanted or premature expulsion of the body from the vagina.

Additionally, the body may be configured to maintain the radial outward force applied even under combined loads applied to the device by the body, for example, inward forces, bending forces along the longitudinal axis, torsional loads (e.g., twisting about the longitudinal axis). The loads applied to the device in use may be static or dynamic, and may be applied, for example, by normal daily activities (e.g., walking, standing, changing body positions), athletic activities (e.g., running, jumping, weight-lifting), coughing, sneezing, or the like. The body may be configured to maintain radial outward force and its expanded configuration without buckling inward when a force causing a torsional displacement of at least about 10 degrees, at least about 20 degrees, at least about 30 degrees, between about 10 degrees and about 20 degrees, between about 10 degrees and about 30 degrees, or between about 20 degrees and about 30 degrees is applied.

Figure 5A:
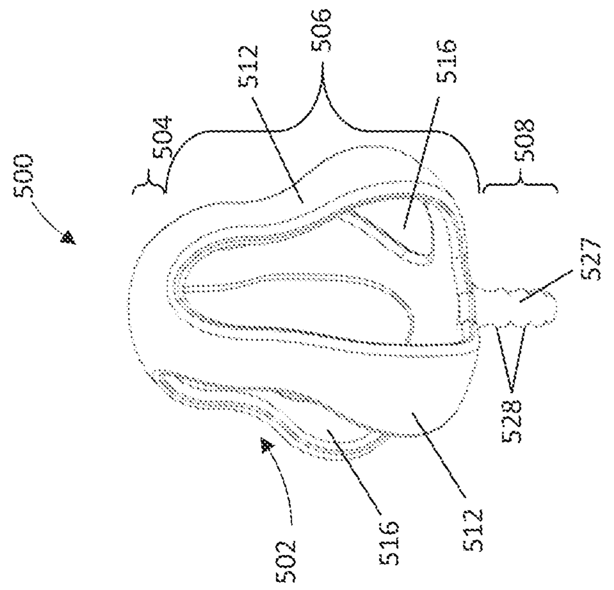
FIGS. 5A-5B depict another variation of a urinary incontinence device.
Figure 5C:
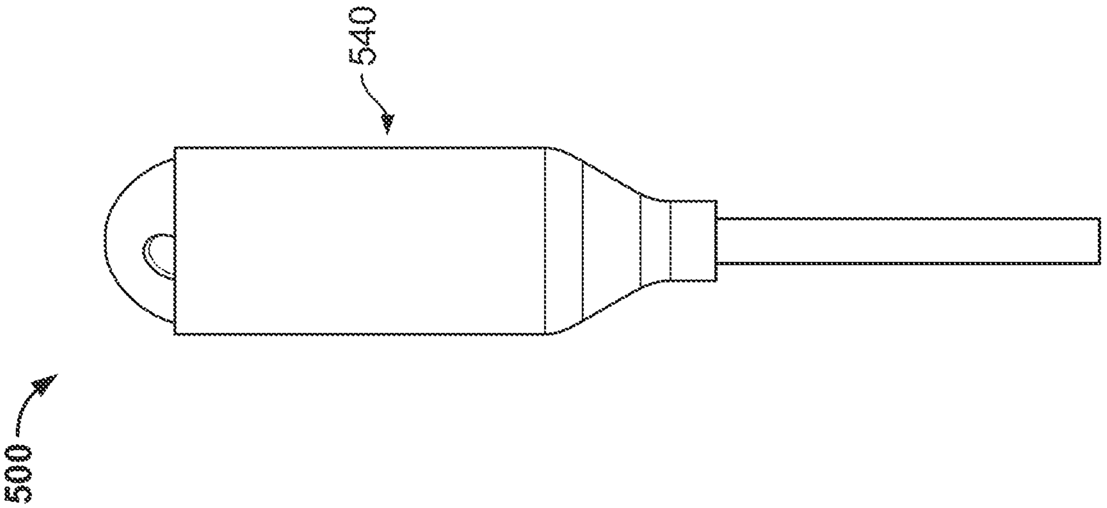
FIG. 5C depicts the urinary incontinence device of FIGS. 5A-5B loaded in an applicator.
Figure 5B:
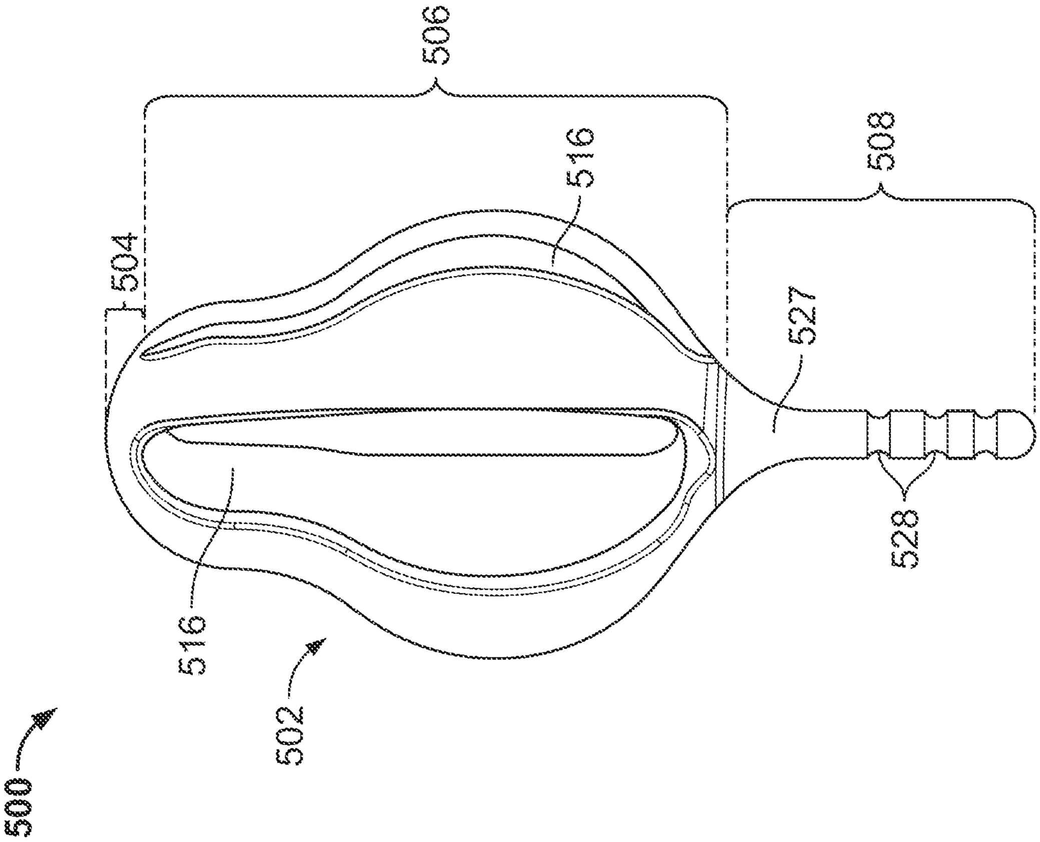

Turning to FIGS. 5A-5C, shown there is an additional variation of the urinary incontinence devices described here. FIGS. 5A and 5B depict perspective views of another variation of a pear shaped urinary incontinence device 500 in an expanded configuration and FIG. 5C depicts the urinary incontinence device 500 in a compressed configuration within an applicator. The urinary incontinence device 500 depicted best in FIGS. 5A and 5B is similar to the urinary incontinence devices described with respect to FIGS. 1A-3F, with like elements labeled with like reference numbers. The incontinence device 500 has a body 502 comprising a proximal portion 504, a central portion 506 comprising a plurality of legs 512 and a plurality of gaps or spaces 516 between and separating the plurality of legs 512, and a distal portion 508. However, in this variation, the proximal portion 504 is much shorter than the proximal portion in the variation described with respect to FIG. 1A. For example, in this variation, the proximal portion 504 may be about 5 mm in length. In this variation, the proximal portion 504 comprises mostly or only the surface and thickness formed by the intersection of the proximal ends of the legs or the proximal end of the body 502. The central portion 506 is longer than the variation depicted in FIG. 1A, and occupies a larger portion of the entire length of the body 502. Additionally, the distal portion 508 comprises a cylindrical or rounded extension 527 or handle instead of a flattened handle. Moreover, instead of an opening, the distal portion 508 comprises one or more (e.g., two, three, four or more) grooves or circular channels 528. It should be appreciated that while not depicted, the distal portion 508 in this variation may alternately or additionally comprise an opening. Additionally in the variation depicted in FIGS. 5A-5B, the first and second bulbous portions are within the central portion 506 and are hollow.

Figure 6B:
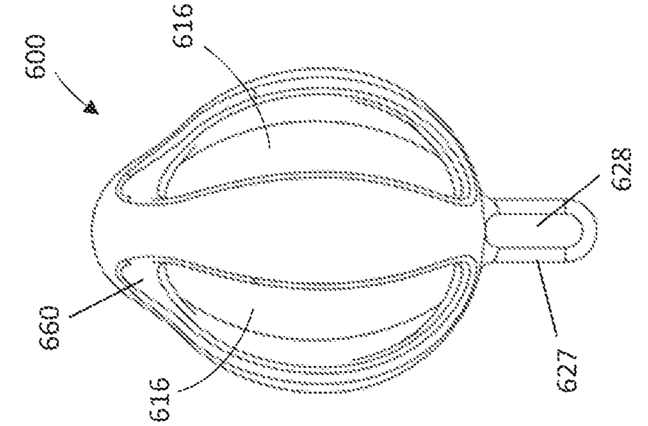
FIGS. 6A and 6B depict a perspective view and a front view, respectively, of another variation of a urinary incontinence device.
Figure 6A:
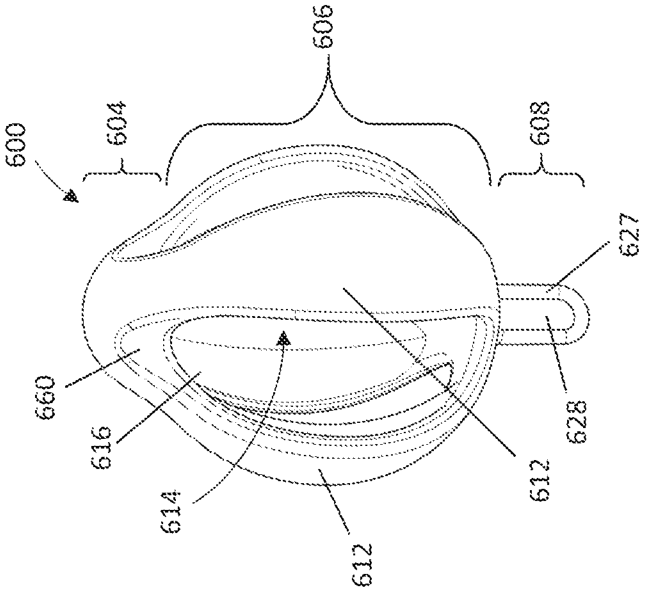

FIGS. 6A and 6B depict perspective and front views of another variation of a pear-shaped urinary incontinence device 600 in an expanded configuration. The urinary incontinence device 600 is similar to the urinary incontinence devices described with respect to FIGS. 1A-3F, with like elements labeled with like reference numbers, but with several structural differences. The urinary incontinence device 600 has a body 602 comprising a proximal portion 604, a central portion 606 comprising a portion of the plurality of legs 612 and a plurality of gaps or spaces 616 between or separating the plurality of legs 612, and a distal portion 608. However, the proximal end of the plurality of legs 612 is in the proximal portion 604 and the proximal portion 604 comprises webbing 660 between the proximal ends of the legs 612. Thus, in this variation, the proximal portion 604 may still be solid, but may include indented, inset, or cut out portions (which form the webbing 660). In some instances, it may useful to utilize a proximal portion 604 with the aforementioned indented, inset, or cut out portions because this may allow the incontinence device to be compressed to a smaller diameter at the proximal end, which may assist in inserting the device (e.g., fitting and/or positioning the device in an applicator for insertion). The central portion 606 may comprise the remainder of the plurality of legs 612, which may form a hollow interior or chamber 614. In the variation depicted here, each of the plurality of legs 612 may have a wedge or triangular cross-sectional shape. Additionally, the distal portion 608 may comprise an elongate extension 627 with an opening 628 that occupies a larger portion or area of the elongate extension 627 than in the variation depicted in FIG. 1A. Thus, in this variation, the elongate extension 627 may form a loop. Furthermore, in the variation depicted in FIGS. 6A-6B, the ratio of the length of the proximal portion 604 to the length of the central portion 606, and the length of the body 602 with and without the distal portion 608 may be smaller (i.e., the proximal portion may be shorter relative to the central portion and the body) than in the variation depicted in FIG. 1A. In some instances, this variation may provide a soft but rigid proximal portion to assist in insertion and the proximal portions of the plurality of legs may provide additional stiffness, which may assist in lifting the bladder and/or locating the device below the sphincter, while still allowing an expanded portion of the device to apply outward force on the urethra.

Force Concentrators

Figures 7A, 7B, 7C:
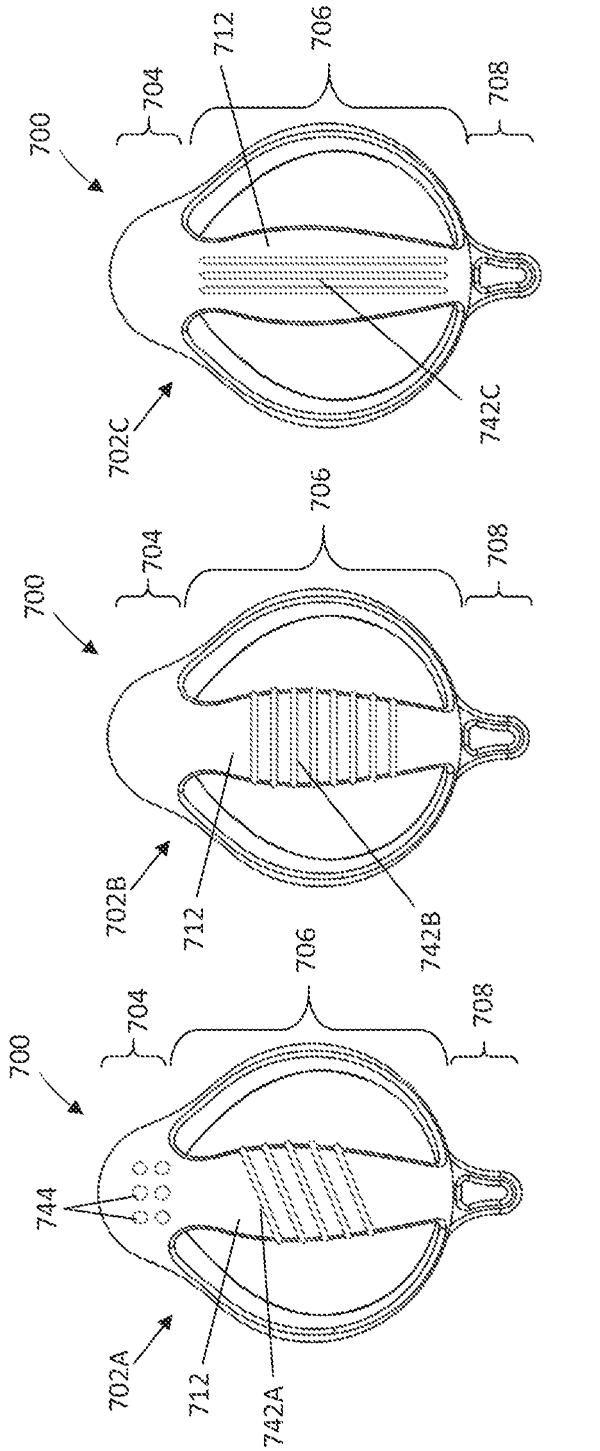
FIGS. 7A-7C depict variations of the urinary incontinence devices described here comprising force concentrators.

Any of the urinary incontinence devices described herein (e.g., any of the variations described with respect to FIGS. 1A-6B) may comprise one or more force concentrators on one or more portions of the body. For example, a depicted in FIGS. 7A-7C, the urinary incontinence device 700 may have a body 702A, 702B, 702C comprising a proximal portion 704, a central portion comprising a plurality of legs 712, a distal portion 708, and one more force concentrators 742A, 742B, 742C. In some variations, the force concentrator 742A, 742B, 742C may comprise a protrusion, ridge, or otherwise raised portion that may act to increase the force or pressure applied to the tissue at or along the force concentrator 742A, 742B, 742C, which may better support or close the urethra without applying unnecessary force or pressure in areas where support or closure is not needed or effective. In some variations, the force concentrator may be linear, while in other variations, the force concentrator may be circular (e.g., a series of round protrusions or bumps) or may comprise another suitable (e.g., atraumatic) shape. The force concentrator may be oriented to provide targeted support to the most effective or useful areas. For example, in some variations, the force concentrator may be located on one or more of the plurality of legs 712, for example, in a proximal region, a central region, and/or a distal region of the legs 712. Additionally, in variations in which the force concentrator may be linear, the force concentrator may be angled relative to the longitudinal axis of one or more of the plurality of legs 712 or of the body 702 (FIG. 7A), may be horizontal or perpendicular to the longitudinal axis of one or more of the plurality of legs (FIG. 7B), or may be vertical or substantially parallel to the longitudinal axis of one or more of the plurality of legs 712 or the body 702 (FIG. 7C). The body 702 may comprise a plurality of force concentrators, for example, two, three, four, five, six, seven, eight, or more, and may comprise force concentrators having a combination of the orientations described above. In variations comprising a plurality of force concentrators, the force concentrators may create a series of pressure points along the urethra, which may increase resistance to flow overall. In some instances, these variations may provide equivalent resistance to flow as compared with devices that provide only a single pressure point, but may provide a reduced pressure at each of the pressure points, which may increase the comfort and safety of the device. In some variations, the force concentrator may extend over one or both of the longitudinal edges of the leg.

It should be appreciated that the force concentrators may also affect the flexibility/rigidity of the body on the portions of the body on which they are located, and thus, may also be used to vary or assist in varying the flexibility/rigidity and/or bending profile of the legs, as described in more detail above. Additionally, when the device is used with an applicator, as will be described in more detail below, the force concentrators may serve to offset or otherwise create space between the surface of the body 702 and the inside surface of the applicator. This may decrease the surface area of the body touching the applicator and thus the frictional force between the applicator and the body, which may make the device easier to advance out of the applicator during insertion.

Frictional Elements

Referring again to FIG. 7A, in some variations, the body may further comprise frictional elements or features 744 configured to hold the device in place and/or resist movement of the body 702 relative to the vaginal tissue once the device 700 is inserted in the body. For example, these elements or features 744 may comprise protrusions, bumps, soft saw teeth, surface roughness, a combination thereof, or the like, which may increase friction with surrounding tissue when the body is inserted. The frictional elements or features 744 may be located on an external surface of the proximal portion 704 (e.g., at a proximal end and/or distal end of the proximal portion 704) and/or on an external surface of one or more of the plurality of legs 712, for example, in a central region where the largest radial force is applied. In some variations, the frictional elements may also serve as force concentrators and vice versa, and/or the body may comprise both frictional elements and force concentrators.

Materials

The urinary incontinence devices described here may comprise a biocompatible material that is suitable for reuse. For example, the urinary incontinence device may comprise a non-absorbent, resilient, and/or flexible material. In some variations, one or more portions (proximal, central, distal) of the body may comprise silicone, thermoplastic (such as, for example, polypropylene (PP) and polyethylene (PE)), thermoplastic elastomer including, for example, thermoplastic vulcanizates, thermoplastic rubber (TPR), thermoset, and/or urethane. In some instances, all portions of the body (e.g., proximal, central, and distal portions) may be formed from or comprise the same materials, while in other variations, different portions of the body may comprise different materials. For example, the proximal portion may comprise a first material, the central portion may comprise a second material, and a distal portion may comprise a third material, and the first, second and/or third materials may be the same as or different from one another. As mentioned above, in some instances the device may comprise a core and a surrounding material, and the material of the core and the surrounding material may differ. For example, in some variations, the device may comprise a metal or injected molded plastic core and a silicone or elastomer surrounding material. In some variations, the device may further comprise texture surfaces (as described above), and/or a surface coating. The devices described here may be formed or manufactured using any suitable method, for example injection molding, rotational molding, casting, liquid injection molding, or the like. In some variations, the device may be formed as a single piece (i.e., the proximal, central, and distal portions may be integrally formed), for example, by casting, injection molding, liquid injection molding, rotational molding, or the like, while in other variations, one or more of the portions of the body may be formed separately and attached to one another using any suitable technique, for example, sewing, stapling, thermoforming, adhesive, bonding, a combination thereof, or the like. In some instances, one or more portions of the body may be formed in a shape other than that of the final shape of the body (for example, with a lesser or greater degree of curvature than the final body), and the final shape may be created by joining the portions of the body together mechanically (e.g., using adhesive bonding, sewing, thermoforming, stapling, a combination thereof, or the like.). This may allow a pre-stressed condition of the device to give the body itself a greater or lesser potential for elastic recoil (or restoring force to resume its preferred shape).

Drug and Energy Delivery

In some variations, the urinary incontinence devices described here may be further configured to deliver drugs and/or energy. For example, in some variations, the urinary incontinence device may further comprise a reservoir and/or the body itself may be impregnated with one or more drugs and may elute or otherwise deliver the drug(s) while implanted within the user. For example, in some variations, the urinary incontinence device may deliver a hormone therapy estrogen (e.g., estradiol), an anti-biotic, anti-microbial, and/or anti-fungal agent, which may treat the user and/or prevent the device from colonization. Additionally, in some instances, the device may further comprise a transducer, which may be used to assist a user in Kegel training by providing bio-feedback.

Reusability

As mentioned above, the urinary incontinence devices described here may be reusable. For example, in some variations, the urinary incontinence devices may be worn for up to twelve hours and may be reusable for three months, six months, nine months, or one year or more after removing the device from its packaging. The device may be provided in a sterile or non-sterile form. In some instances, the device may be reusable for between one and three months, three and six months, between three and nine months, between six and nine months, or between nine months and one year. The device may be configured to be easily cleaned (e.g., it may have few, if any, indentations, nooks, crannies, small channels, or other small openings) that may be difficult to access while cleaning. Additionally, as mentioned above, a portion of the device may be hollow, which may allow access to the internal surfaces of the device for cleaning. In variations in which the device further comprises a removal/retrieval string, the string may be disposable. In some variations, the device is dishwasher safe.

II. Kits

In some instances, the urinary incontinence devices described here may be combined with additional items to form a kit or system. For example, in some variations, the kit or system may comprise a urinary incontinence device (e.g., a urinary incontinence device with any combination of the features described herein) and an applicator. The kit or system may further comprise a cleanser, e.g., alcohol wipes, and/or cleaning liquids, foams, tablets or powders (such as effervescent tablets or powders), or gels (such as water based anti-bacterial foam, liquid, or gel containing, for example, alcohol) and/or instructions for use. Additionally or alternatively, in some instances the kit or system may comprise a vented container for steam cleaning (e.g., a steam cleaning bag). In some variations, the system or kit may comprise a plurality of incontinence devices (e.g., two, three, or more) and/or a plurality of applicators (e.g., two, three, four, or more). In these variations, the kits or systems may be designed to last a user an extended period of time, for example, six months, a year, eighteen months, two years, or longer, depending on the reusability of the device and/or applicators and the number of devices/applicators included. In some instances, the systems or kits may comprise a plurality of incontinence devices and each of the incontinence devices may have a different characteristics (e.g., the devices may be different sizes such as small, medium, and large, may have different shapes and/or may be made from different materials such that they may provide different levels of support to the urethra and/or bladder to optimally fit women with varying anatomy (e.g., size, degree of tissue elasticity, pelvic floor strength). In some variations, the systems or kits may comprise one or more (e.g., a plurality, a one month supply, a three month supply, a six month supply, or more) removal strings or other flexible elongate members used as an aid for retrieval. When removal strings are used, they may be made of suitable material, for example, cotton, polyester, nylon, a combination thereof, or the like.

In some variations, the system or kit may be packaged with the urinary incontinence device pre-loaded in the applicator, while in other variations, the urinary incontinence device may be separate from the applicator. The urinary incontinence device and/or applicator may be contained in a sterilized or unsterilized package. In some variations, the systems and kits may further comprise a drying container (e.g., a bag or rigid container) that may allow for evaporation through the container such that the incontinence device and/or applicator may be placed in the container wet after cleaning. For example, in some variations, the material of the container may be porous enough to allow for drying and may provide lint and particle protection for cleanliness. Exemplary materials include, but are not limited to, woven and non-woven fabrics, cotton, polyester, rayon, silk, thermoplastic, thermoset, at combination thereof, or the like. Additionally or alternatively, in some instances, the systems or kits may further comprise a storage container (e.g., a box or bag) configured to prevent contamination after the incontinence device is washed/dried. In some variations, the same container may be used for both drying and storage (i.e., the drying container may be the storage container). In some instances, the systems or kits may further comprise a discrete travel container, for example, a container shaped as another item users may commonly carry such as lipstick, make-up, tampon holders, or the like.

Applicator

Figures 8A, 8B, 8C:
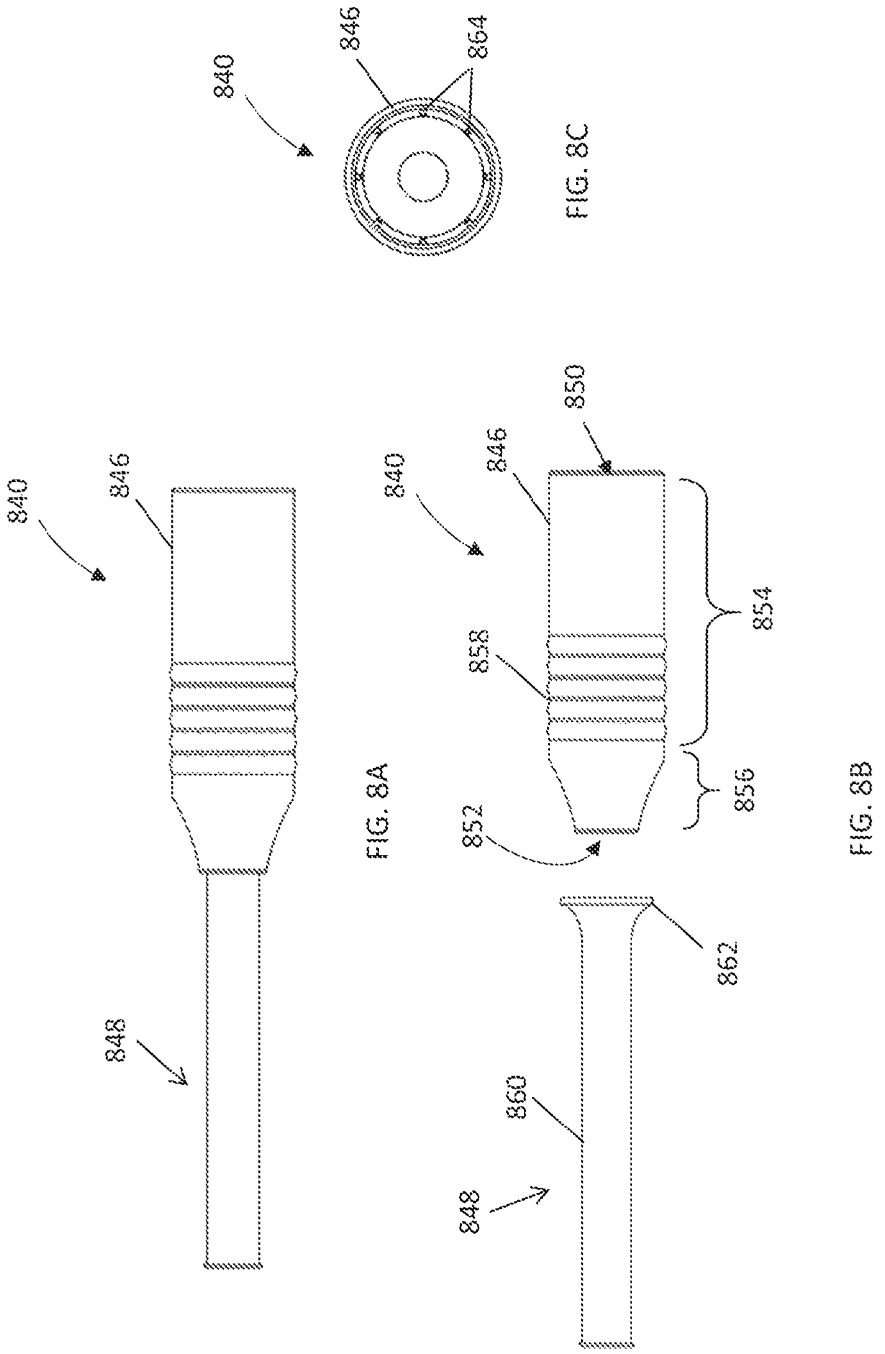
FIGS. 8A-8C depict assembled, disassembled, and top views, respectively, of an applicator for use with the urinary incontinence devices described here.

As mentioned above, in some variations, a system or kit may comprise an applicator or delivery device, which may assist a user in inserting the device. FIGS. 8A-8C depict an assembled view, an exploded view, and a top view, respectively, of an illustrative applicator 840. The applicator 840 may comprise a base 846 and a plunger 848, each comprising a lumen therethrough. The base 846 may comprise a proximal opening 850, a distal opening 852, a proximal portion 854, and a distal portion 856. The proximal portion 854 may be configured to constrain or otherwise hold the incontinence device in the compressed configuration for insertion, while the distal portion 856 may be configured to hold a portion of or otherwise couple to the plunger 848. The proximal portion 854 may begin at the proximal opening 850 and may be coupled to the distal portion 856, which may end at the distal opening 852. The proximal portion 854 may be cylindrical with a constant diameter and the distal portion 856 may be distally tapered such that the diameter of the proximal end of the distal portion 856 is equal to the diameter of the proximal portion 854 and the proximal opening 850, while the diameter at the distal end is smaller than the diameter of the proximal end and is equal to the diameter of the distal opening 852. The proximal portion 854 may further comprise a grip 858, which may comprise ridges, grooves, dimples, protrusions, a surface pattern, a combination thereof, or the like. The grip 858 may assist a user to holding the base 846 during insertion of the device and may provide the user with an indication of where the applicator should be held for effective insertion and/or for proper insertion depth. In some variations, the plunger 848 may be solid and may not comprise a lumen therethrough.

In some variations, an internal surface of the base 846 may comprise one or more ridges or raised portions 864, which may decrease friction between the external surface of the body of the device and the internal surface of the base 846. In some variations, the ridges or raised portions 864 may be circular or semi-circular (e.g., circumferentially or partially circumferentially surround the cavity/lumen in the proximal and/or distal portion 854, 856) of the base 846, or axial/linear (e.g., parallel to the longitudinal axis of the applicator 840). The ridges or raised portions 864 may be positioned on all or a portion of the proximal and/or distal portions 854, 856 of the base 846 and may be continuous or discontinuous. The base 840 may comprise any number of ridges or raised portions 864, for example, one, two, three, four, five, six, seven, eight, between two and four, between four and six, between six and eight, or more than eight. In some variations, the internal surface of all or a portion (e.g., the proximal portion 854, the distal portion 856) of the base 846 may comprise a surface coating (e.g., a lubricous coating) or may be treated with a lubricant that may decrease friction between the external surface of the body of the incontinence device and the base 840.

The plunger 848 may comprise a cylindrical, elongate body 860 and a proximal flange 862. The proximal flange 862 may have a diameter that is greater than the diameter of the elongate body 860. In some variations, the proximal flange 862 may be cupped or rounded such that it may better hold a distal end of the incontinence device during insertion. For example, a proximal surface of the proximal flange 862 may be concave and may have a radius of curvature that mimics the radius of curvature of the distal end of the central portion of the incontinence device such that the plunger may maintain contact with the device as it is inserted (e.g., pushed past the pelvic floor muscles).

The distal end of the base 846 may be releasably coupled to a proximal end of the plunger 848. In some variations, the base 846 and the plunger 848 may snap together, while in other variations, the plunger 848 may be slideably positioned through the distal opening 852 of the base 846 without the use of additional connectors. The proximal flange 862 of the plunger 848 may be positioned within the tapered distal portion 852 of the base 846 adjacent to the distal opening 852 when the applicator is assembled. The proximal flange 862 may abut the incontinence device when the device is positioned within the lumen or cavity in the base 846 and may push the device to advance the device out of the applicator 840 and deploy the device. The assembled length of the applicator 840 may be such that a portion of the base 846 may be inserted into the vagina far enough to position the incontinence device between the bladder and the pelvic floor while a user may still grasp a portion of the base 846 and advance the plunger 848. For example, in some variations, the length of the base 846 may be between about 6 cm and about 8 cm, between about 6 cm and about 7 cm, or about 6.35 cm, and the length of the plunger may be between about 8 cm and about 9 cm, between about 7 cm and about 8 cm, or about 7.8 cm. The assembled length of the applicator may be between about 12 cm and about 13 cm, or about 12.7 cm.

While depicted as separate pieces, in some variations, the base 846 and the plunger 848 may be a single piece or may be coupled together such that they may not be released from one another easily. In some instances, however, it may be useful for the base 846 and the plunger 848 to be releasably connectable as this may allow the base 846 and the plunger 848 to be separated for easier cleaning. In some variations, one end of the plunger 848 may comprise a small bead or protrusion (e.g., molded into the plunger 848) such that the base 846 and the plunger 848 may snap together with such that they remain coupled throughout normal use, but may be separated by hand for cleaning. The base 846 and the plunger 848 may be made from any suitable materials, for example, polypropylene, polyethylene, ABS, a rigid plastic, or the like. In some variations, the base 846 and/or plunger 846 may be molded. In some variations, the applicator 840 may be reusable, for example, for three months, six months, eight months, a year or more. Additionally, in some instances, the applicator 840 may further comprise a removal device (e.g., a hook) that may catch on an opening in the distal portion and/or between the plurality of legs of the incontinence device. In these variations, the applicator 840 may also be used to assist a user in removing the device once it is inserted. In some embodiments, the external surface of the applicator 840 may comprise a surface coating (e.g., a lubricous coating) that decreases friction between an external surface of the applicator (e.g., the base 846) and tissue, which may facilitate advancement of the applicator 840 into the vaginal canal.

III. Methods

Also described here are methods of treating urinary incontinence, for example, stress urinary incontinence, in a user having a vagina and a pelvic floor. Methods of treating urinary incontinence generally comprise one of the urinary incontinence devices described herein into the vagina to close the urethra and/or lift the bladder neck, which may treat or otherwise aid in treating urinary incontinence. In some variations, methods may further comprise loading the urinary incontinence device (e.g., any of the urinary incontinence devices described herein) into an applicator (e.g., any of the applicators described herein) and advancing the urinary incontinence device out of the applicator and into the vagina. Methods may further comprise removing the incontinence device from the vagina, re-loading the incontinence device into the applicator, and reinserting the applicator into the vagina.

Figure 9C:
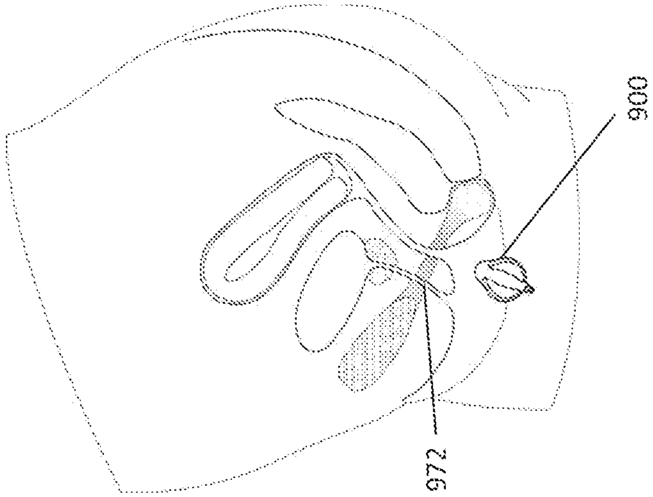
FIGS. 9A-9C provide illustrative representations of certain aspects of the methods for treating urinary incontinence described here.
Figure 9B:
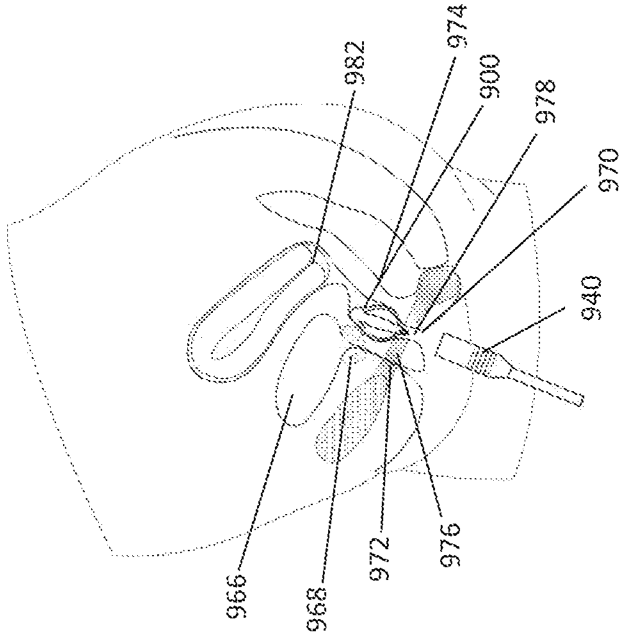
Figure 9A:
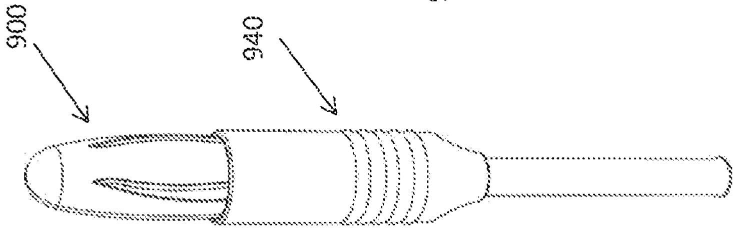

FIGS. 9A-9C depict some of the steps of the methods described here. For example, FIG. 9A depicts loading a urinary incontinence device 900 into an applicator 940. In some variations, the urinary incontinence device 900 may be loaded or otherwise positioned within the applicator 940 after it is removed from a package. In other variations, as mentioned above, the urinary incontinence device 900 may be pre-loaded into the applicator 940. In variations of the method where the incontinence device 900 has been previously used and is being reused, the urinary incontinence device 900 may be cleaned and dried or otherwise removed from a drying rack or bag and positioned within the applicator 940. Moreover, in variations in which a retrieval/removal string or other flexible elongate member may be used, the retrieval member may be positioned within an opening of the distal portion of the incontinence device or around one or more of the legs through the gaps between the legs before loading the device into the applicator. Once the urinary incontinence device 900 is positioned within the application 940, it may be held at least partially inside the applicator 940 in a compressed, delivery configuration. Put another way, loading the urinary incontinence device 900 into the applicator 940 may transition the urinary incontinence device 900 from an expanded configuration to a compressed configuration. The urinary incontinence device 900 may be positioned within the applicator 940 such that the distal portion or the distal end of the central portion of the device abuts or is otherwise adjacent to the proximal flange of the applicator. A proximal portion or the proximal end of the urinary incontinence device may be adjacent to or partially extending through the proximal opening of the applicator base.

After the urinary incontinence device 900 is loaded into the applicator 940, the applicator 940 may be inserted into the vagina 978 (FIG. 9B). More specifically, a proximal end of the base and thus a proximal end of the urinary incontinence device 900 may be advanced through the vaginal opening 970 and into the vaginal canal until the device is properly positioned for deployment (e.g., the proximal end of the application may be inserted about 3.5 cm into the vagina). For example, in some variations, the applicator 940 may be advanced until the grips on the base of the applicator are adjacent to an external surface of the vaginal opening 970. The plunger of the applicator 940 may then be pushed or otherwise advanced to move the incontinence device 900 proximally relative to the applicator base and out of the proximal opening of the applicator base. Once the incontinence device 900 has been advanced out of the proximal opening of the applicator base and thus out of the applicator 940, the incontinence device 900 may no longer be constrained by the applicator and may thus expand radially outward (e.g., the central portion, the plurality of legs may extend radially outward) to the expanded or deployed configuration. The incontinence device may self-expand to the expanded configuration.

The incontinence device 900 may be advanced out of the applicator to appropriately position the incontinence device to apply a closure and/or lifting force once in the expanded configuration. For example, in some variations, the incontinence device may be advanced out of the applicator to position a proximal portion of the device just below the bladder 966 and beneath the cervix 982, for example, at or near the urethra sphincter 968 and the posterior urethra-vesical angle 974, and a distal end of the device past or above the pelvic floor 976. In some variations, the incontinence device may apply a closure and/or lifting force between about 3 cm and about 7 cm into the vagina. Once advanced out of the applicator 940 and in the expanded configuration, the incontinence device 900 may apply a closure force to the urethra 972 and/or a lifting force to the bladder 966. Put another way, once in the expanded configuration, the closure device may push against the urethra 972 to close the urethra or otherwise inhibit urine from traveling therethrough (as depicted in FIG. 9B). The applicator 940 may then be retracted or otherwise removed from the vagina 978. Moreover, in variations in which the incontinence device comprises one or more force concentrators, the incontinence device may be positioned such that the force concentrators apply a localized, targeted, and/or additional force to a portion of the urethra. For example, the incontinence device may be positioned such that the force concentrators act on a region of the urethra that is not protected by the sphincter or pelvic floor (where a second sphincter is located). Once in the expanded configuration, the diameter of at least a portion of the incontinence device, for example, the central portion, may be larger than the vaginal opening 970 such that the incontinence device may remain in the delivered position during activity, including, for example, high stress activities such as sneezing, running or other forms of high intensity exercise.

Figure 9E:
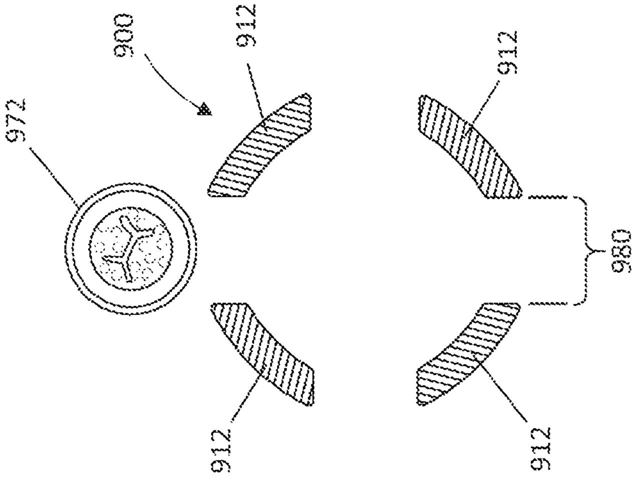
FIGS. 9D and 9E depict variations of an inserted urinary incontinence device.
Figure 9D:
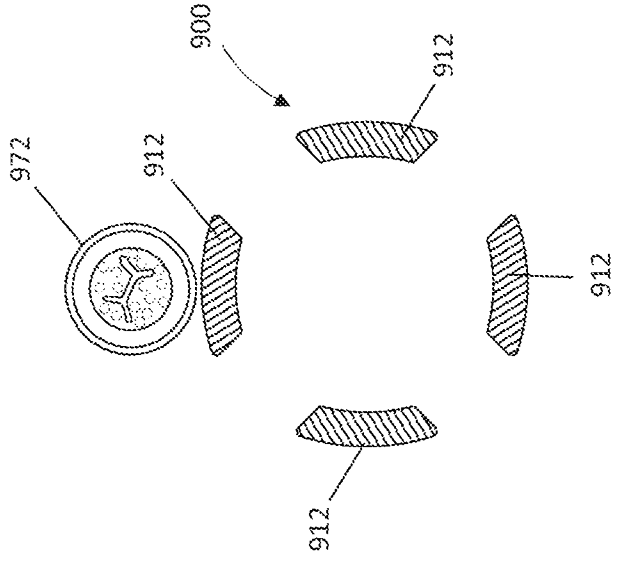

In some variations, the incontinence device may self-orient (e.g., rotationally about the longitudinal axis of the device) relative to the urethra sphincter 968, the urethra 972, and/or other portions of the female anatomy. For example, in some variations, the urinary incontinence device 900 or a portion thereof (e.g., a central portion, the plurality of legs 912) may cradle the urethra 972, and thus apply lateral force to the urethra 972, as depicted in FIG. 9E. For example, the width 980 of one or more of the gaps between the plurality of legs 912 may be sized such that the urethra 972 may fit at least partially therein. For example, in some variations, the width 980 may be between about 15 mm and about 20 mm, between about 15 mm and about 18 mm, or between about 20 mm and about 40 mm. In some instances, the width 980 may be about 18 mm. In other variations, the width 980 may be smaller, for example, about or at least 6 mm. Additionally or alternatively, in some embodiments, the shape and/or curvature of one or more of the plurality of the legs may assist in self-orienting the incontinence device. In these embodiments, the width may be between about 0 mm (i.e., the device may be completely compressed or nearly completely compressed) and about 3 mm, between about 1 mm and about 3 mm, or between about 2 mm and about 3 mm. In other variations, the urinary incontinence device 900 or a portion thereof (e.g., a central portion, one or more of the plurality of legs) may apply a direct force to the urethra 972 to close the urethra, as depicted in FIG. 9D.

Figure 10C:
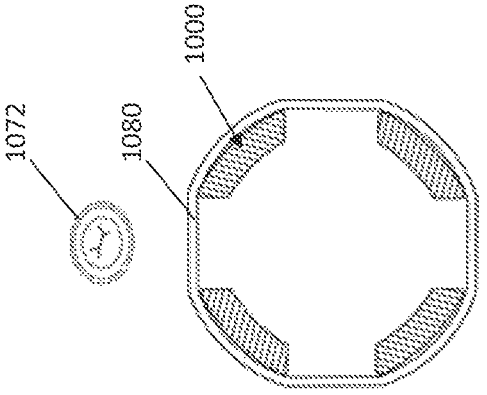
FIG. 10A depicts a vaginal canal and urethra prior to insertion of an incontinence device and FIGS. 10B-10C depict a vaginal canal and urethra after insertion of a variation of the incontinence devices described here.
Figure 10B:
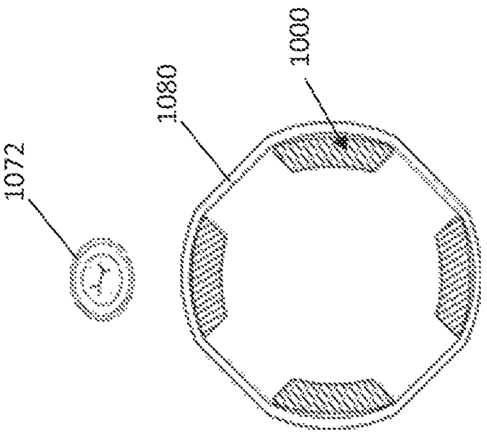
Figure 10A:
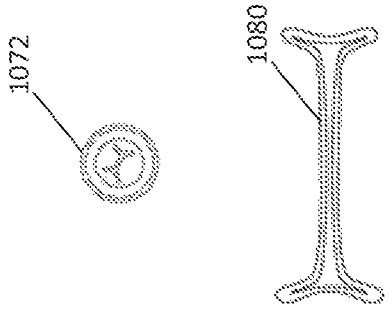

FIG. 10A depicts a vaginal canal 1080 and urethra 1072 prior to insertion of an incontinence device, while FIGS. 10B-10C depict different inserted positions of the incontinence device 1000. In particular, FIG. 10B depicts an incontinence device 1000 within the vaginal canal 1080 that provides direct support to the urethra 1072 to close the urethra 1072, while FIG. 10C depicts an incontinence device 1000 within the vaginal canal 1080 that provides lateral support to the urethra 1072 to close the urethra 1072. As mentioned above, in some variations, the incontinence device may self-orient (e.g., rotate around its longitudinal axis). In these variations, the incontinence device 1000 may move from the position depicted in FIG. 10B (or from another insertion position) to the position depicted in FIG. 10C without additional user intervention. Put another way, in some variations, regardless of the position of the incontinence device 1000 upon insertion, the incontinence device 1000 may self-orient (e.g., rotate or otherwise move) to the position shown in FIG. 10C.

As mentioned above, the incontinence devices (and applicators) described here may be configured to be reusable. Accordingly, after a desired use period (e.g., up to two hours, two hours, up to four hour, four hours, six hours, eight hours, twelve hours, between two and four hours, between four and eight hours, between four and twelve hours, between six and eight hours, between six and twelve hours, between eight and twelve hours), the methods described here may further comprise one or more of the following: removing the incontinence device from the vagina, for example, using the distal retrieval portion, washing the incontinence device, re-loading the incontinence device into the optionally reusable applicator, reinserting the applicator with the same incontinence device into the vagina, and reinserting the incontinence device into the vagina. In some variations, the same applicator may be used for both initial insertion and any number of subsequent insertions. In these variations, the methods may further comprise washing the applicator between uses. In some variations, for example those in which the device is used during exercise (e.g., a jog, an exercise class) or another specific activity (e.g., attending an event), the device may be inserted prior to the activity and removed after the activity such that the desired use period corresponds to the length of the activity (e.g., up to one hour, up to two hours, up to three hours, between 30 minutes and one hour, between one hour and two hours, or the like).

In some variations, the incontinence device may be removed from the vagina by pulling on the distal retrieval portion of the incontinence device with a user's fingers, while in other variations, a retrieval string or member or other retrieval device (e.g., an application with a hook as described above) may be used to assist a user in accessing and removing the incontinence device. Once the incontinence device is removed, the incontinence device no longer applies the closure and/or lifting force to the urethra and/or bladder respectively, and the urethra may thus return to its pre-treatment position (FIG. 9C). In variations in which the incontinence devices described here may comprise a drug or an energy source, the methods may further comprise delivering the drug and/or stimulation energy while the incontinence device is in use or otherwise positioned within the vagina.

Although the foregoing invention has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

The invention claimed is:

1. A vaginal device comprising:
- a body configured to be inserted into a vagina, wherein the body comprises:
  - a solid proximal insertion portion; and
  - a central portion comprising a hollow chamber formed from a plurality of legs extending distally from the solid proximal insertion portion to a distal surface and defining the hollow chamber of the central portion, wherein the hollow chamber is unobstructed along a central longitudinal axis of the body from the solid proximal insertion portion to the distal surface, and
  - wherein the body further comprises a compressed configuration and an expanded configuration, and wherein in the expanded configuration, a length of the central portion is at least three times a length of the proximal insertion portion along the central longitudinal axis of the body.

2. The device of claim 1, wherein a cross-sectional dimension of each of the plurality of legs varies along the central longitudinal axis of the body.

3. The device of claim 1, wherein each of the plurality of legs has a same triangular cross-sectional shape.

4. The device of claim 1, wherein a width of each of the plurality of legs varies along the central longitudinal axis of the body.

5. The device of claim 4, wherein the width of each of the plurality of legs decreases along the central longitudinal axis from a central point of each leg to a distal end of each leg.

6. The device of claim 1, wherein a thickness of each of the plurality of legs varies along the central longitudinal axis of the body.

7. The device of claim 6, wherein the thickness of each of the plurality of legs decreases along the central longitudinal axis from a central point of each leg to a distal end of each leg.

8. The device of claim 1, wherein the body further comprises a lateral cross-sectional diameter, and wherein the lateral cross-sectional diameter is largest at a widest point of each of the plurality of legs.

9. The device of claim 1, wherein the device further comprises a distal retrieval portion coupled to the distal surface.

10. The device of claim 9, wherein a length of the solid proximal insertion portion is about ¼ a length of the body in the expanded configuration without the distal retrieval portion.

11. The device of claim 9, wherein the distal retrieval portion is integrally formed with the distal surface.

12. The device of claim 9, wherein the distal retrieval portion comprises a handle configured to be grasped by a user for removal of the device from the vagina.

13. The device of claim 9, wherein the distal retrieval portion comprises an opening configured to assist a user in grasping the device for removal.

14. The device of claim 9, wherein the distal retrieval portion comprises a flat, elongate structure.

15. The device of claim 1, wherein the device is configured to deliver one or more of a hormone therapy agent, an antibiotic agent, an anti-microbial agent, and an anti-fungal agent.

16. The device of claim 1, wherein the device is configured to self-orient within the vagina after insertion.

17. The device of claim 1, wherein the device is formed from silicone.

18. A vaginal device comprising:
- a body configured to be inserted into a vagina, the body comprising:
  - a proximal insertion portion; and
  - a central portion comprising a hollow chamber formed from a plurality of legs extending distally from the proximal insertion portion to a distal surface and defining the hollow chamber of the central portion, wherein the hollow chamber is unobstructed along a central longitudinal axis of the body from the proximal insertion portion to the distal surface, and
  - wherein a thickness of each of the plurality of legs varies along the central longitudinal axis of the body.

19. The device of claim 18, wherein the thickness of each of the plurality of legs decreases along the central longitudinal axis from a central point of each leg to a distal end of each leg.

20. The device of claim 18, wherein a width of each of the plurality of legs varies along the central longitudinal axis of the body.

* * * * *